(12) United States Patent
Yamada et al.

(10) Patent No.: US 10,551,387 B2
(45) Date of Patent: Feb. 4, 2020

(54) CANCER CELL DETECTION METHOD USING LIVING BODY-DERIVED CELLS

(71) Applicant: Hirosaki University, Hirosaki-shi (JP)

(72) Inventors: Katsuya Yamada, Hirosaki (JP); Ayako Sasaki, Hirosaki (JP); Kouki Ono, Hirosaki (JP); Kiyoshi Tone, Hirosaki (JP)

(73) Assignee: HIROSAKI UNIVERSITY, Hirosaki-shi (JP)

( * ) Notice: Subject to any disclaimer, the term of this patent is extended or adjusted under 35 U.S.C. 154(b) by 201 days.

(21) Appl. No.: 15/513,259

(22) PCT Filed: Sep. 24, 2015

(86) PCT No.: PCT/JP2015/076900
§ 371 (c)(1),
(2) Date: Jun. 14, 2017

(87) PCT Pub. No.: WO2016/047676
PCT Pub. Date: Mar. 31, 2016

(65) Prior Publication Data
US 2017/0315129 A1    Nov. 2, 2017

(30) Foreign Application Priority Data
Sep. 24, 2014    (JP) .................. 2014-193424

(51) Int. Cl.
*G01N 33/58*    (2006.01)

(52) U.S. Cl.
CPC .................. *G01N 33/582* (2013.01)

(58) Field of Classification Search
CPC ............... C12Q 1/34; C12Q 2521/301; C12Q 2523/115; C12Q 2525/101; C12Q 2527/125; C12Q 2537/164; C12Q 1/66; C12Q 1/26; C12Q 1/6827; C12Q 1/683; C12Q 1/68; C12Q 1/6806; C12Q 1/6809; C12Q 1/6897; C12Q 2565/201; C12Q 1/04; C12Q 1/025; C12N 9/14; C12N 9/0069; C12N 11/00; C12N 9/96; C12N 9/1051; C12N 9/22; C12N 2533/30; C12N 2502/28; C12N 2513/00; C12N 5/0068; C12N 5/062; C12N 5/0657; C12N 2533/50; C12N 2533/52; C12N 2533/54; C12N 2533/56; C12N 2537/10; C12N 5/0606; C12N 5/0691; C12Y 308/01005; C12Y 113/12005; C12Y 308/01; G01N 33/581; G01N 2333/914; G01N 33/573; G01N 33/5308; G01N 2333/47; G01N 2333/4709; G01N 33/48; G01N 33/577; G01N 33/582; G01N 33/5008; G01N 33/54373; G01N 2333/71; G01N 2333/726; G01N 2500/10; G01N 33/5011; G01N 33/566; G01N 33/569; G01N 33/56966; G01N 33/57438; G01N 33/74; G01N 33/553; C07K 7/06; C07K 16/00; C07K 17/622; C07K 2319/43; C07K 2319/61; C07K 2299/00; C07K 14/47; C07K 2319/80; C07K 2319/81; C07K 14/4711; C07K 14/705; C07K 16/18; C07K 2317/24; C07K 2317/34; C07K 2317/92; C07K 5/0202; C07K 5/06078; C07K 7/02; C07K 7/08; C07K 9/00; C07K 14/78; C09B 11/24; C09B 1/00; C09B 23/04; C09B 23/06; C09B 23/105; Y10S 530/825; Y10S 530/815; B82Y 30/00; B82Y 10/00; B82Y 5/00; C07H 19/06; C07H 21/00; C12P 19/18; C12P 19/30;
(Continued)

(56) References Cited

U.S. PATENT DOCUMENTS 6,172,261 B1 *    1/2001    Vermeulin ............ C07C 233/36
                                                            506/15
7,160,923 B1 *    1/2007    Vermeulin ............ C07C 233/36
                                                            514/311
(Continued)

FOREIGN PATENT DOCUMENTS

| JP | H07-027682 A | 1/1995 |
| JP | 2012029752 A1 | 3/2012 |
| WO | 2012133688 A1 | 10/2012 |

OTHER PUBLICATIONS

Nature New Biology, vol. 244, Jul. 18, 1973, see pp. 83-84. 1973.*
(Continued)

*Primary Examiner* — Deborah K Ware
(74) *Attorney, Agent, or Firm* — Kratz, Quintos & Hanson, LLP

(57) ABSTRACT

A cancer cell detection method that makes it possible to perform imaging of cells in a living state and a dual detection method for cancer cells in which the aforementioned method is combined with a pre-existing dyeing method for cytodiagnosis. The method uses living body-derived cells and includes: incubating living cells included in a sample taken from a person together with a fluorescently-labeled L-glucose derivative and detecting the fluorescently-labeled L-glucose derivative that is taken up into the cells; and detecting fluorescence emitted by the L-glucose derivative that is present within the cells while the cells are attached to a thin glass or plastic plate. Also provided is a dual detection method for cancer cells in which the cancer cell detection method that uses living body-derived cells is combined with a dyeing method using cells that are fixed using an alcohol or the like.

17 Claims, 11 Drawing Sheets

(58) Field of Classification Search
CPC .......... C12P 19/34; Y02P 20/52; A61K 38/00; A61K 47/50; A61K 2039/55505; A61K 2039/575; A61K 2039/6081; A61K 39/0007; A61K 49/0004; A61K 2300/00; A61K 6/083; A61K 31/722; A61K 33/42; A61K 38/1825; A61K 38/1841; A61K 38/1858; A61K 38/1875; A61K 38/30; A61K 6/0023; A61K 35/12; A61K 49/221; A61K 49/223; A61K 35/34; A61K 35/36; A61K 35/44; C07C 233/36; C07C 233/40; C07C 233/78; C07C 235/20; C07C 235/34; C07C 235/50; C07C 237/10; C07C 237/20; C07C 237/22; C07C 271/20; C07C 271/22; C07C 9/1411; C07C 9/65234; C07C 9/6561; C12M 3/00; C12M 21/08; C12M 25/02; A61L 27/34; A61L 27/3839; A61L 27/46; A61L 2430/14; A61L 27/3804; A61L 27/3813; A61L 27/3886; A61L 2300/252; A61L 2300/404; A61L 2300/414; A61L 2300/606; A61L 24/0063; A61L 27/3604; A61L 27/3895; A61L 27/54; A61F 2002/183; A61F 2310/00365; A61F 2/18; A61F 2/02; C08L 33/08; C08L 33/10; C08L 39/06; C08L 3/20; C08L 5/08; C08L 77/04; C08L 89/00; F24S 50/20; H01L 31/02021; H01L 31/0521; H01L 31/0543; H01L 31/0547; H01L 31/0549; H02S 20/32; Y02E 10/52; B01J 19/0046; B01J 2219/00527; B01J 2219/00637; B01J 2219/00644; B01J 2219/0072; B01J 2219/00725; B01J 2219/00743; B22F 1/0025; B22F 1/025; C22C 5/02; C23C 16/0281; C23C 16/06; C40B 30/06; Y10T 428/12771

See application file for complete search history.

(56) References Cited

U.S. PATENT DOCUMENTS

2013/0157287 A1  6/2013  Takanashi
2014/0154717 A1  6/2014  Yamada

OTHER PUBLICATIONS

International Search Report for International Application No. PCT/JP2015/076900 dated Dec. 22, 2015.

G. Pratx, et al.; "High-Resolution Radioluminescence Microscopy of 18F-FDG Uptake by Reconstructing the 3-Ionization Track", The Journal of Nuclear Medicine, vol. 54, No. 10, Oct. 2013, pp. 1841-1846, XP55467098, US (7 Sheets).

A. Sturzu, et al.; "Rhodamine-marked bombesin: a novel means for prostate cancer fluorescence imaging", Investigational New Drugs, Martinus Nijhoff Publishers, Boston, US, vol. 32, No. 1, Jun. 1, 2013, pp. 37-46, XP035906191 (10 Sheets).

Z. Cheng, et al.; "Near-Infrared Fluorescent Deoxyglucose Analogue for Tumor Optical Imaging in Cell Culture and Living Mice", Bioconjugate Chemistry, American Chemical Society, US, vol. 17, Apr. 21, 2006, pp. 662-669, XP003012182 (8 Sheets).

Extended European search report issued to EP Patent Application No. 15844697.1, dated Apr. 26, 2018 (9 Sheets).

T. Yamamoto, et al.; "Syntheses of 2-NBDG analogues for monitoring stereoselective uptake of D-glucose;" Bioorganic & Medicinal Chemistry Letters 21; 2011; pp. 4088-4096 and cover sheet (10 Sheets total).

* cited by examiner

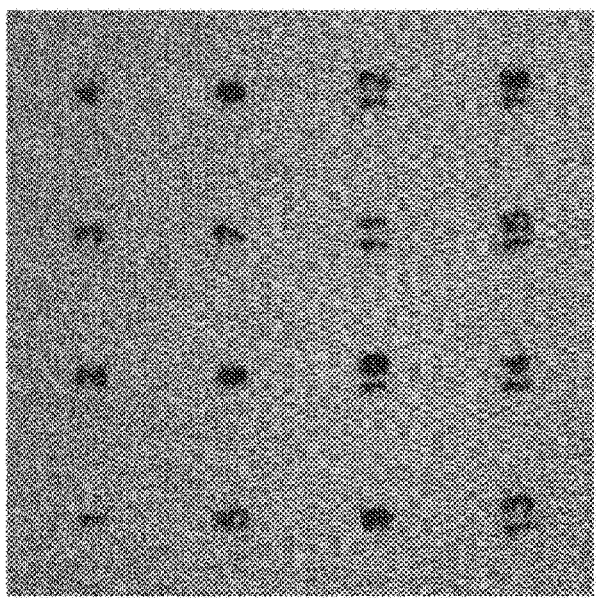
Fig. 1B
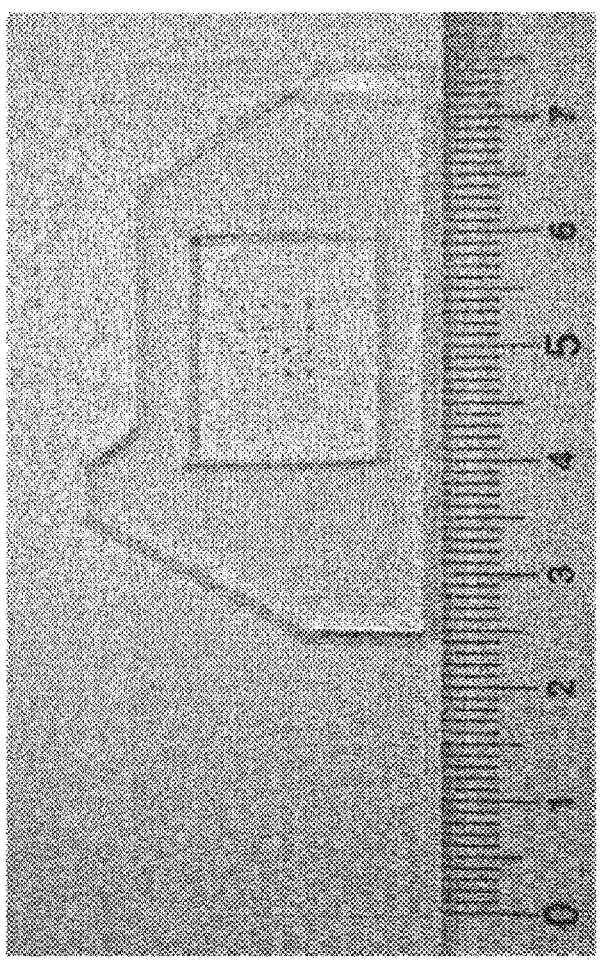
Fig. 1A
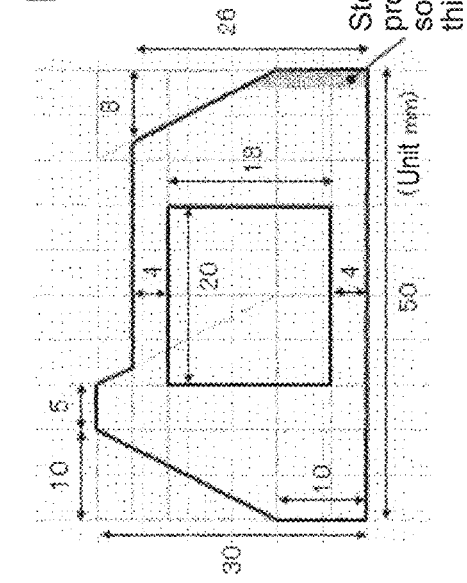
Fig. 1D
Fig. 1C

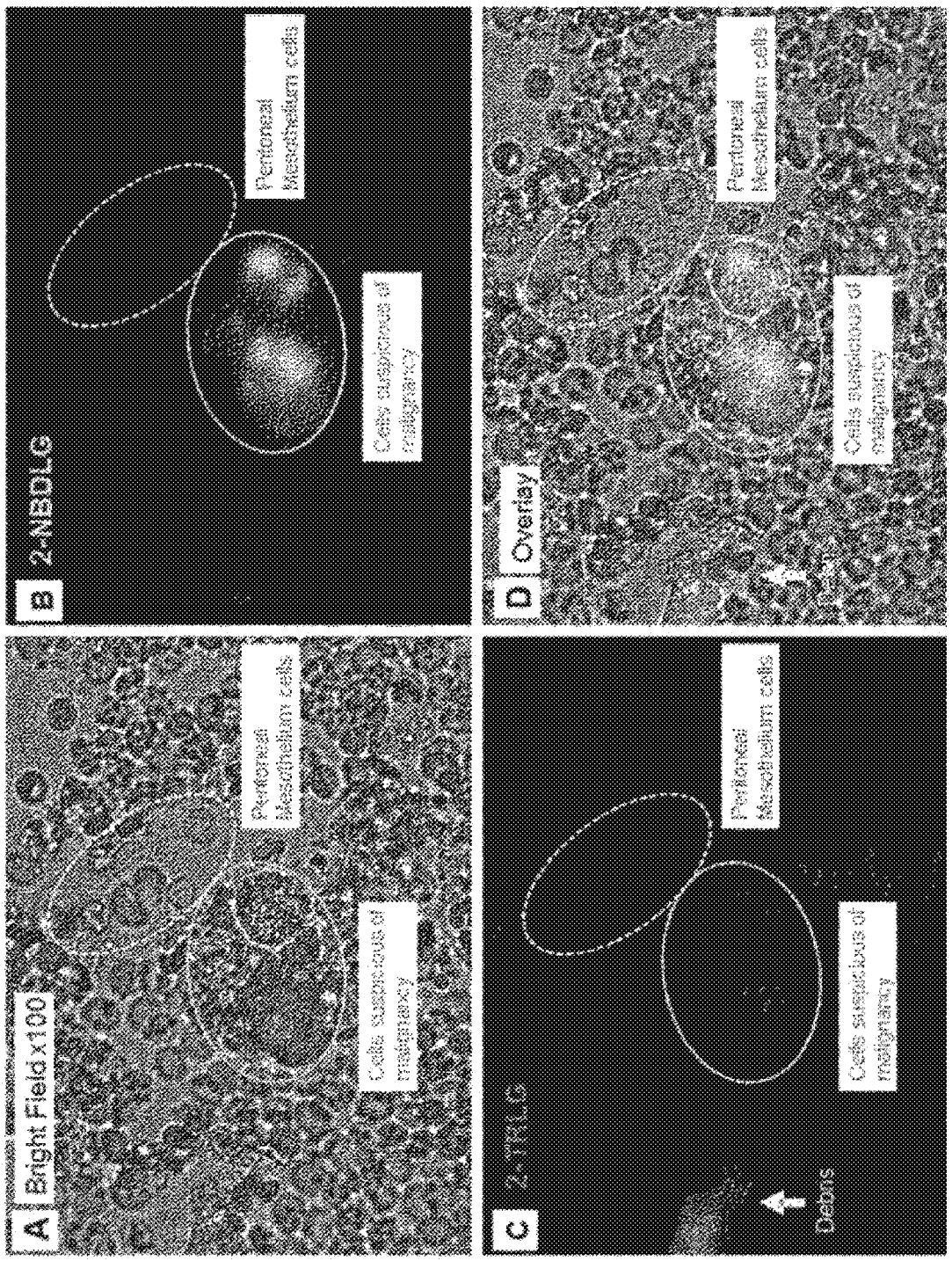
Fig. 2 Live-cell imaging of ascites obtained from an ovarian cancer patient

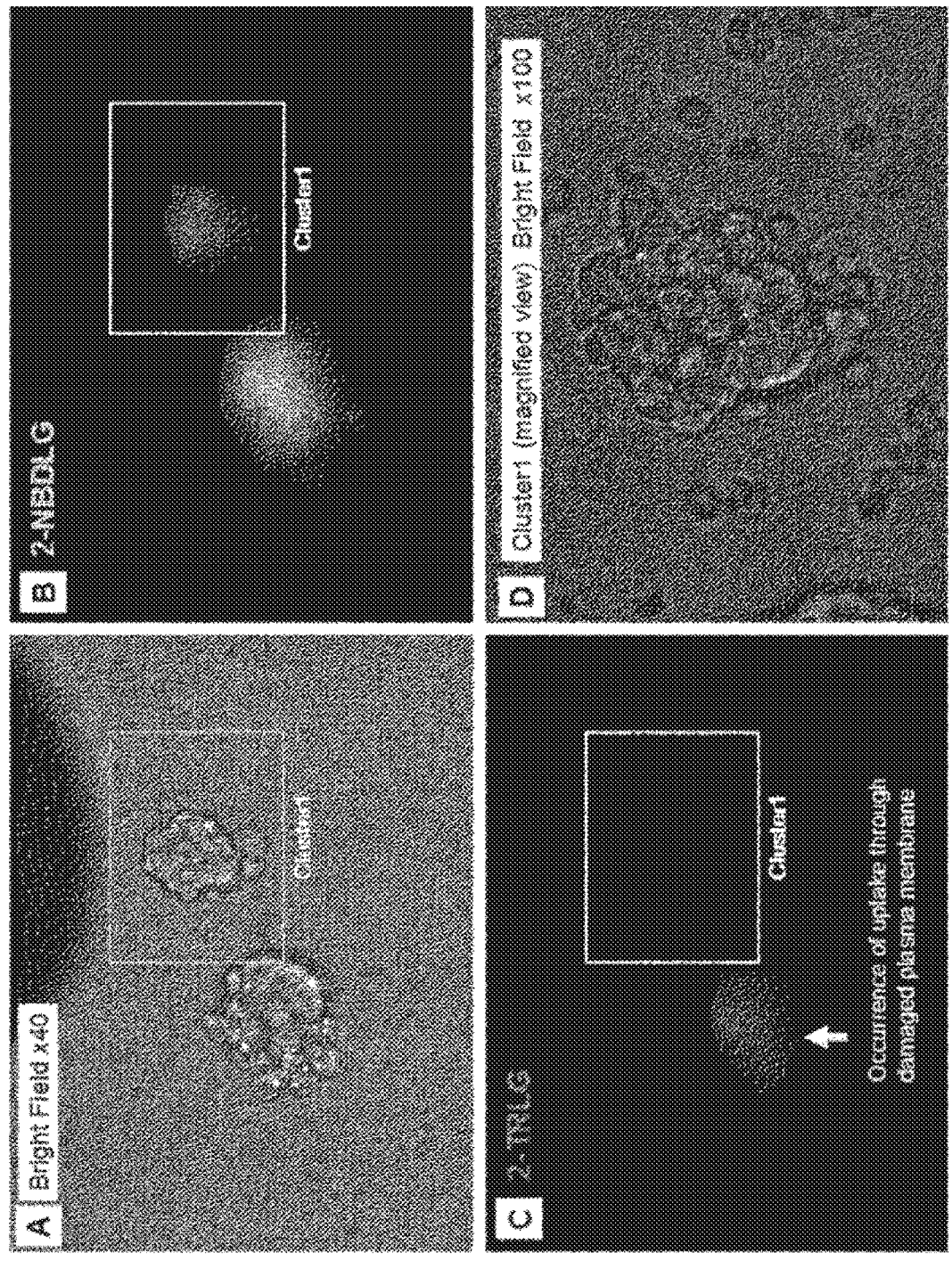

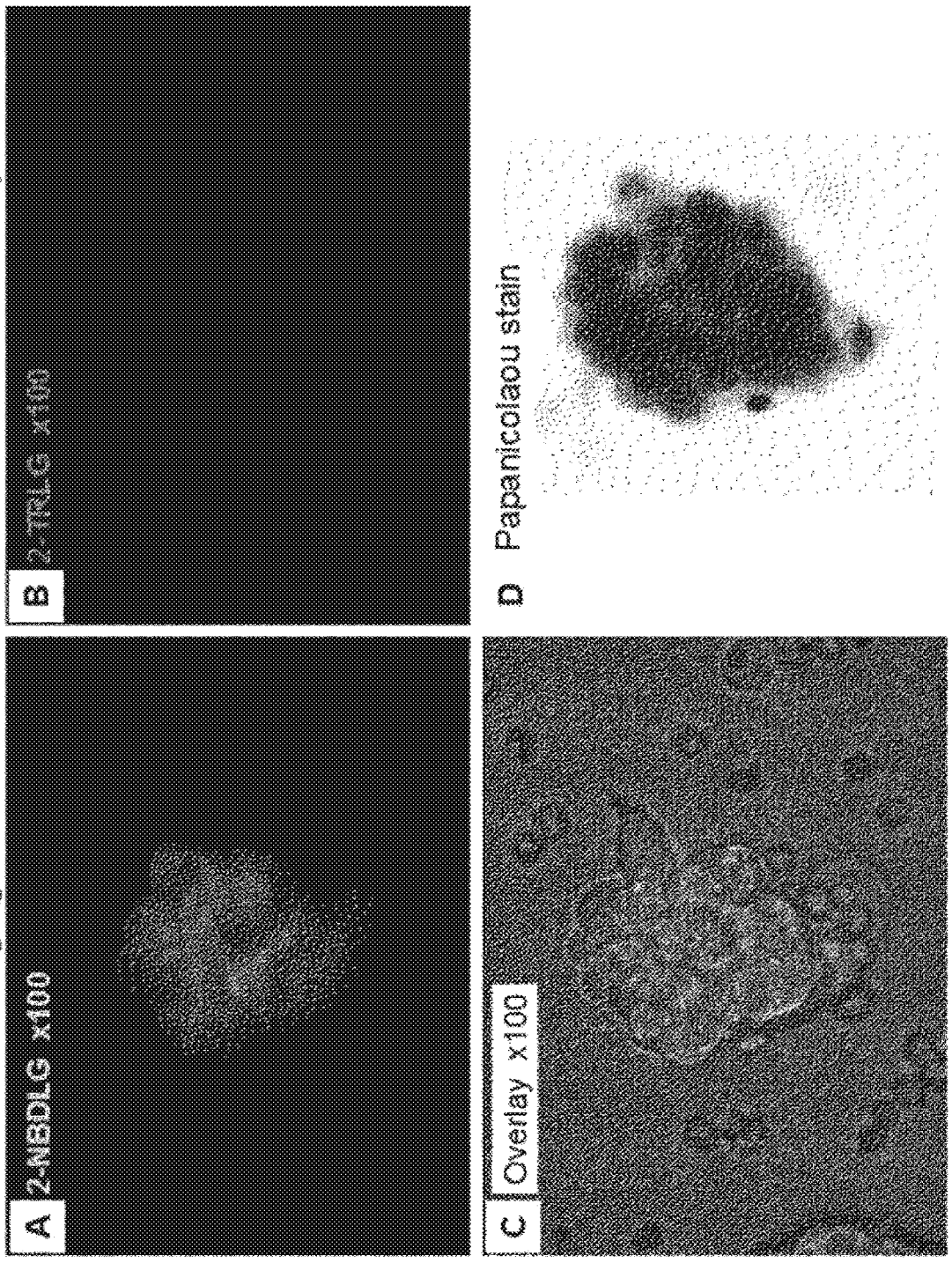
Fig. 4 Live-cell imaging of ascites obtained from a uterine cancer patient

CANCER CELL DETECTION METHOD USING LIVING BODY-DERIVED CELLS

TECHNICAL FIELD

The present invention relates to a method of detecting cancer cells among living body-derived cells, and particularly relates to a method of detecting cancer cells using a fluorescently labeled L-glucose derivative. The present invention also relates to a glass-slide set for cell-adhesion/observation which can be used with the above method of detecting cancer cells.

BACKGROUND ART

At the present day, a half of the population in Japan suffers from cancer. However, if cancer is accurately diagnosed in the early stage and appropriately treated, better prognosis and QOL would be expected in many cases. Whether cells are cancer cells or not is determined as follows: cells (cytological diagnosis) or tissues (histological diagnosis) are taken from a suspected cancer site, observed by a cytotechnologist or a board certified cytopathologist for the presence of morphological anomalies, and diagnosed based on their experience and subjectivity. However, an early stage of cancer called a precancerous lesion or a borderline lesion called Class III may be difficult to be diagnosed when using the morphological approach alone. Indeed, these may result in disagreed interpretation among cytotechnologists or pathologists, or suspending of judgment in order to schedule a re-examination. When re-examined, patients may find that their cancer had continued to progress. Therefore, development of a method of evaluating cells which is more objective and definite than the present method is demanded for the sake of all of patients, pathologists, cytotechnologists, clinicians, and laboratory test providers.

Accurate diagnosis of borderline lesions is an earnest wish in clinical practice, and a serious issue which may change patients' future. Further, the conventional cytological diagnosis in which cells are morphologically observed one by one requires years of experience. Hence, training programs have been failing to provide necessary personnel in a timely fashion, resulting in increased workload on site and missed cases of cancer. These have been recognized as problems to be solved for years.

In a laboratory test for the identification of cancer, the less invasive "cytological diagnosis" (a laboratory test for the presence of cellular atypia including the N/C ratio, polarity, nuclear morphology and the like, and structural atypia in accumulation of cells and the like) is first performed to detect cancer cells solely based on morphology. When cancer cells or cells suspected to be cancerous are detected, histological diagnosis which is capable of providing a more detailed identification is performed, and the results therefrom are used to decide on a treatment strategy.

Further, "cytological diagnosis" is frequently used for the purposes of: conveniently examining the presence of cancer at medical checkup and the like; examining the presence of dissemination over peritoneum, pleura, and the like by withdrawing a coelomic fluid such as an ascitic fluid or a pleural fluid during a cancer operation or for diagnosis; or detecting the presence of cancer such as tumors in the urinary system by testing urine. In cases where histological diagnosis cannot be performed, such as when an ascitic fluid, a pleural fluid and the like are tested, or when the presence of renal pelvis cancer is investigated, and the like, cytological diagnosis needs to be performed to decide on a treatment strategy.

In Japan, except for in some advanced institutions, cytological diagnosis is commonly performed as follows: a sample taken from a patient is smeared onto a glass slide, fixed with alcohol, and then stained and embedded. Cell morphology is then observed under a microscope. Cytological diagnosis can be performed quickly and conveniently, but cytotechnologists dedicated for the tests are required to examine one by one a large number of cells contained in every glass slide for morphological and nuclear anomalies repeatedly every day. Years of experience and skills are required to find cancer cells quickly and reliably without missing any.

Moreover, if cancer cells, no matter how few they are, are found within the accumulated cell populations, the test concludes that the sample has cancer. Since overlooking of cancer cells may lead to a delay in accurate diagnosis, concentration, patience, and skills for finding cancer cells without missing any are required. However, it cannot be denied that such abilities of cytotechnologists may vary between individuals.

In addition, for cells suspended in an ascitic fluid or urine, target cells for observation are present in a state where they are detached from the original tissues. Such cells are away from supplies of blood flows and nutrition, becoming more susceptible to cell degeneration. Therefore, it is not uncommon that these cells undergo morphological changes to have densely stained nuclei, increased. N/C ratios (nucleus/cytoplasm ratios), or the like, resulting in difficulty in distinguishing them from cancer cells. These cells may be classified as so-called Class III for which benign-malignant discrimination is difficult, hindering decision making on the treatment strategy, resulting in watch-and-wait or re-examination. Further, the range of classification of Class III may vary depending on the experience and subjectivity of individual cytotechnologists and board certified cytopathologists. This may delay the start of treatment to the detriment of patients. However, the current cytological diagnosis relying solely on morphological information is obviously less than satisfactory for solving the aforementioned problems.

Moreover, in some cases, observation under a light microscope cannot provide a clear view of target cells due to the presence of a large amount of blood cells, hindering accurate diagnosis. In order to improve this situation, the liquid-based cytological diagnosis (LBC) has been proposed as a method of preparing a sample. Although LBC is useful for reducing human factors in preparing specimens, there is a report stating that it fails to produce significant difference in benign-malignant discrimination over the conventional method.

Whether cells are cancer cells or not is conventionally determined by cytotechnologists and board certified cytopathologists based on the following morphological characteristics of cells, among others:
1) an increased ratio of nucleus to cytoplasm (the N/C ratio);
2) anomalies in cell morphology, including the position of nucleus in a cell and the morphology of nucleus chromatin;
3) anomalies in the clustering conditions of cells (structural atypia).

However, such diagnosis relying on morphological anomalies is made based on the subjectivity of cytotechnologists and board certified cytopathologists. Therefore, cells may not be diagnosed when they are at the borderline between benign and malignant, or may not be able to be diagnosed solely based on cell morphology. As described above, diagnosis based on subjectivity may provide different results depending on opinions of observers, or may result in inconclusive results. As one example, there is 10% or more Class III classification in tests for recurrence of bladder cancer. This is a serious problem that needs solving.

Logically speaking, although specimens classified as Class III would be either cancerous or non-cancerous, the distinction between "cells being suspicious for malignancy" and "cells not being suspicious for malignancy" is not discrete. As such, in order to reduce Class III, there are demands for an objective measure which can be used in place of the current cytological diagnosis which has a subjective aspect as described above, or well-defined indexes which can allow for determination without relying on amount of experience.

Further, in view of the current situation where anomalies are visually searched by skilled cytotechnologists one by one when a large number of laboratory tests for cytological diagnosis requiring immediate attention are piled up every day, a guideline for reliably finding anomalies is required in order to avoid false negatives due to overlooking, of cancer.

Immunocytochemical staining may be performed, when determination by common staining such as Papanicolaou stain, Giemsa stain and the like, which are used as the conventional method of cytological diagnosis of cancer, needs to be supplemented. However, no single antibody can provide benign-malignant discrimination on its own, and thus multiple antibodies are required to be combined. Even in that case, decisive benign-malignant discrimination will be difficult.

In addition, it is noted that the current cytological diagnosis is solely based on "morphologically detectable anomalies" of dead cells fixed by alcohol, and is not a method for observing "functional anomalies of cells" which may not necessarily be manifested as morphological changes. Common cytological diagnosis alone cannot determine whether or not a cell in a specimen is functionally normal even if it looks like normal cell morphology. For example, a cell, which is morphologically indistinguishable from a normal cell, may already be infected with a virus having a high risk of subsequent cancerization, or may already show an abnormal cell function. If that is the case, definitive diagnosis cannot be obtained until morphological anomalies are clearly observed. This may delay the start of treatment due to repeated tests, resulting in a detriment of patients.

The present inventors have developed 2-[N-(7-nitrobenz-2-oxa-1,3-diazole-4-yl)amino]-2-deoxy-L-glucose (2-NBDLG), a green fluorophore NBD-labeled, novel derivative of non-naturally occurring L-glucose, which does not bind to a glucose transporter GLUT. Further, the present inventors have found that 2-NBDLG visualizes cancer cells due to its specific uptake into them, when administered to in vitro culture cells such as pancreatic cancer cells or to cancer-bearing mice, allowing for imaging of a cancer cell cluster consisting of cancer cells with various cell states (Patent Document 1).

The present inventors also have developed 2-amino-2-deoxy-L-glucose (2-TRLG), a plasma membrane-impermeable fluorescent L-glucose derivative bearing a red fluorophore sulforhodamine 101 being attached at position 2 via a sulfonamide bond. Further, in experiments in vitro where 2-TRLG and 2-NBDLG are applied to cultured cells, the present inventors have found that both 2-NBDLG and 2-TRLG are taken up into cells having damaged plasma membranes as well as cells showing nonspecific uptake such as phagocytosis, allowing for discrimination of cells which have taken up 2-NBDLG only (Patent Document 1).

Patent Document 1: PCT International Publication No. WO2012/133686
Non Patent Document 1: Yamamoto et al., Bioorg. Med. Chem. Lett. 21:4088-4096, 2011

DISCLOSURE OF THE INVENTION

Problems to be Solved by the Invention

An object of the present invention is to provide a novel method of detecting cancer cells among living body-derived cells, which can be used for cytological diagnosis. Another object of the present invention is to provide a method of live imaging of cancer cells among living body-derived cells, which can be combined with an existing method of cytologically diagnosing cancer cells such as the Papanicolaou staining method and the Giemsa staining method.

Means for Solving the Problems

After conducting extensive studies in view of the above situation, the present inventors have found that a region capable of holding a buffer solution provided on a thin glass or plastic plate enables living body-derived cells to be attached to and held on the thin glass or plastic plate. The present inventors have also found that an effect for preventing cell dehydration can be significantly enhanced by providing a hydrophobic region of a water-repellent material such as silicone in the above buffer-solution holding region. Further, the present inventors find that the above effect enables a fluorescently labeled molecule to be taken up by a cell while maintaining the cell in a viable state to detect fluorescence from the fluorescently labeled molecule inside the cell. Thus, an aspect of the present invention has been completed. The above method enables live-cell imaging of living body-derived cells, and also enables detection of cancer cells among the living body-derived cells by using a specific fluorescently labeled molecule. Further, the above method of detecting cancer cells by live imaging may be combined with an existing method of cytologically diagnosing cancer cells such as the Papanicolaou staining method and the Giemsa staining method to provide a method for dual detection of cancer cells. Thus, another aspect of the present invention has been completed.

Exemplary aspects of the present invention will be described below.

(1) A method of detecting cancer cells among living body-derived cells, including steps of:
(a) incubating living cells contained in a sample taken from a human with a fluorescently labeled L-glucose derivative, the fluorescently labeled L-glucose derivative being an L-glucose derivative having a 7-nitrobenz-2-oxa-1,3-diazole group or a derivative thereof as a fluorophore on the molecule thereof,
(b) stopping intracellular uptake of the L-glucose derivative,
(c) allowing the cells to attach on a thin glass or plastic plate, the plate having a region for holding a buffer solution for maintaining the cells in a viable state on a surface thereof, and
(d) detecting fluorescence from the L-glucose derivative present inside a cell while maintaining the cells attached to the plate in a viable state.
(2) The detection method according to (1), in which the fluorescently labeled L-glucose derivative is a mixture of L-glucose derivative having a 7-nitrobenz-2-oxa-1,3-diazole group or a derivative thereof as a fluorophore on the molecule thereof and 2-amino-2-deoxy-L-glucose (2-TRLG) in which a sulforhodamine 101 is attached via a sulfonamide bond at position 2.

(3) The detection method according to (2), further including a step of determining the degree of damage on the plasma membrane of a fluorescently imaged cell with reference to a fluorescence color tone of the cell when detecting fluorescence in step (d).

(4) The detection method according to any one of (1) to (3), in which the L-glucose derivative having a 7-nitrobenz-2-oxa-1,3-diazole group or a derivative thereof as a fluorophore on the molecule thereof is 2-[N-(7-nitrobenz-2-oxa-1,3-diazole-4-yl)amino]-2-deoxy-L-glucose (2-NBDLG).

(5) The detection method according to any one of (1) to (4), in which the incubation in step (a) is performed at a temperature of 22 to 37.5° C. for 3 to 15 minutes.

(6) The detection method according to any one of (1) to (5), in which the step of stopping intracellular uptake of the fluorescently labeled L-glucose derivative in step (b) is performed by treating the cells with a buffer solution free from the fluorescently labeled L-glucose derivative at 0° C. to 5° C.

(7) The detection method according to any one (1) to (6), including performing centrifugation to attach the cells on the plate in step (c), and adding a buffer solution to the region immediately after the centrifugation.

(8) The detection method according to any one of (1) to (7), in which the plate has a thickness of 0.3 mm or less.

(9) The detection method according to any one of (1) to (8), further including allowing a buffer solution to be sufficiently held in the region by using a buffer-solution holding structure configured to enclose the region on the plate, in which the buffer-solution holding structure is a plate-like or ring-like structure having an opening corresponding to the region, and has a thickness sufficient to hold the buffer solution.

(10) The detection method according to (9), in which the buffer-solution holding structure is made of silicone, and has a thickness of 0.5 to 10 mm.

(11) The detection method according to any one of (1) to (10), in which the living body-derived cells are originated from a cell suspension, exfoliative denuded cells, or fine-needle aspirated cells of a patient.

(12) The detection method according to (11), in which the living-body derived cells are originated from a cell suspension selected from expectoration, urine, ascitic fluid, pleural fluid, pericardial fluid, cerebrospinal fluid, bile, pancreatic fluid, synovial fluid, or blood of a patient.

(13) The detection method according to (12), in which the living body-derived cells are originated from an ascitic fluid of a patient having ovarian cancer or endometrial cancer.

(14) A method for dual detection of cancer cells, including detection of the cancer cells by using a fluorescently labeled L-glucose derivative and detection of the cancer cells based on Papanicolaou staining, Giemsa staining, PAS staining, Grocott staining, or immunocytochemical staining, the method including:

performing the detection method according to any one of (1) to (13), and then performing Papanicolaou staining, Giemsa staining, PAS staining, Grocott staining, or immunocytochemical staining using the glass or plastic plate on which the cells are attached, and then comparing cancer cells detected based on fluorescence with cancer cells detected based on Papanicolaou staining, Giemsa staining, PAS staining, Grocott staining, or immunocytochemical staining.

(15) The detection method according to (14), having for showing positional information about the cells on a side opposite to a cell-attaching side.

(16) The method for dual detection of cancer cells according to (14) or (15), including detection of cancer cells by using a fluorescently labeled L-glucose derivative and detection of cancer cells based on Papanicolaou staining.

(17) A method for live-imaging of living body-derived cells by fluorescence, the method including the steps of:
(A) incubating living cells contained in a sample taken from a human with a fluorescently labeled compound,
(B) stopping of intracellular uptake of the fluorescently labeled compound,
(c) allowing the cells to attach on a thin glass or plastic plate, the plate having a region for holding a buffer solution to maintain the cells in a viable state on a surface thereof, and
(D) detecting fluorescence from the fluorescently labeled compound present inside a cell while maintaining the cells attached to the plate in a viable state.

(18) The method for live-cell imaging according to (17), in which the step of stopping intracellular uptake of the fluorescently labeled compound in step (B) is performed by treating the cells with a buffer solution free from the fluorescently labeled compound at 0° C., to 5° C.

(19) The method for live-cell imaging according to (17) or (18), including performing centrifugation to attach the cells on the plate in step (C), and adding a buffer solution to the region immediately after the centrifugation.

(20) The method for live-cell imaging according to any one of (17) to (19), in which the plate has a thickness of 0.3 mm or less.

(21) The method for live-cell imaging according to any one of (17) to (20), further including allowing a buffer solution to be sufficiently held in the region by using a buffer-solution holding structure configured to enclose the region on the plate, in which the buffer-solution holding structure is a plate-like or ring-like structure having an opening corresponding to the region, and has a thickness sufficient to hold the buffer solution.

(22) The method for live-cell imaging according to (21), in which the buffer-solution holding structure is made of silicone, and has a thickness of 0.5 to 10 mm.

(23) The method for live-cell imaging according to any one of (17) to (22), in which the living body-derived cells are originated from a cell suspension, denuded cells, or fine-needle aspirated cells of a mammal.

(24) The method for live-cell imaging according to (23), in which the living-body derived cells are originated from a cell suspension from a human.

(25) A glass or plastic plate for observing living cells with a fluorescence microscope on which cells in a viable state are allowed to attach, the plate having a region for holding a buffer solution to maintain the cells in a viable state on a surface thereof, and the plate having a thickness of 0.3 mm or less.

(26) The glass or plastic plate for cell observation according to (25), further having markings for showing positional information about the cells on a side opposite to a cell-attaching side.

(27) A buffer-solution holding structure for allowing a buffer solution to be sufficiently held in the region, the structure being configured to enclose the region on the plate according to (25) or (26), in which the structure has a plate-like or ring-like shape, and has an opening corresponding to the region, and is made of silicone, and has a thickness of 0.5 to 10 mm.

(28) A plate set for cell observation for observing living cells with a fluorescence microscope, including the glass or plastic plate according to (25) or (26) and the buffer-solution holding structure according to (27).

Further exemplary aspects of the present invention will be described below.

[1] A method for dual detection of cancer cells in a sample taken from a human, the method including:

(a) a method of detecting cancer by fluorescence imaging of living cells contained in the sample, including the steps of: incubating the cells with a fluorescently labeled L-glucose derivative, the L-glucose derivative having a 7-nitrobenz-2-oxa-1,3-diazole group or a derivative thereof as a fluorophore on the molecule thereof, and detecting the intracellularly uptakes fluorescently labeled L-glucose derivative, and detecting fluorescence from the L-glucose derivative present inside a cell while allowing the cells to attach on a thin glass or plastic plate, the plate having a region for holding a buffer solution to maintain the cells in a viable state on a surface thereof, and the detection of fluorescence from the L-glucose derivative present inside the cell being indicative of the cell being cancerous, and (b) a method of detecting cancer based on staining of cells fixed with a fixative such as alcohol or formalin, the method including a step of:

immersing the plate into the fixative such as ethanol or formalin to fix the cells, and then performing staining by any one method selected from the group consisting of Papanicolaou staining, Giemsa staining, PAS staining, Grocott staining, and immunocytochemical staining to detect cancer cells.

[2] The method according to [1], in which the method a of detecting cancer by fluorescence imaging includes the steps of:

(a-1) incubating the living cells contained in the sample taken from the human in a buffer solution containing the fluorescently labeled L-glucose derivative to allow for uptake of the L-glucose derivative, (a-2) replacing the buffer solution with a buffer solution free from the fluorescently labeled L-glucose derivative to stop the uptake of the L-glucose derivative, (a-3) allowing the cells to attach to a cell-attaching region on the thin glass or plastic plate, and adding a buffer solution to a buffer-solution holding region for holding the buffer solution configured to include and enclose the cell-attaching region and provided on the plate, and maintaining the cells in a viable state, the buffer-solution holding region including a plate side for cell adhesion and a buffer-solution holding structure configured to enclose the buffer-solution holding region, (a-4) detecting fluorescence from the L-glucose derivative present inside a cell, and (a-5) detecting cancer cells based on the detection of fluorescence.

[3] The method according to [1], in which the method a of detecting cancer by fluorescence imaging includes the steps of:

(a-1) allowing the living cells contained in the sample taken from the human to attach to the cell-attaching region on the thin glass or plastic plate, (a-2) adding a buffer solution to a buffer-solution holding region for holding the buffer solution configured to include and enclose the cell-attaching region and provided on the plate, and maintaining the cells in a viable state, the buffer-solution holding region including a plate side for cell adhesion and a buffer-solution holding structure configured to enclose the buffer-solution holding region, (a-3) replacing the buffer solution with a buffer solution containing the fluorescently labeled f-glucose derivative, and then incubating the cells attached on the plate to allow for uptake of the L-glucose derivative, (a-4) replacing the buffer solution with a buffer solution free from the fluorescently labeled L-glucose derivative to stop the uptake of the L-glucose derivative, and detecting fluorescence from the L-glucose derivative present inside the attached cells, and (a-5) detecting cancer cells based on the detection of fluorescence.

[4] The method for dual detection of cancer cells according to any one of [1] to [3], in which the fluorescently labeled L-glucose derivative is a mixture of 2-[N-(7-nitrobenz-2-oxa-1,3-diazole-4-yl)amino]-2-deoxy-L-glucose (2-NBDLG) and 2-amino-2-deoxy-L-glucose (2-TRLG) in which sulforhodamine 101 is attached at position 2 via a sulfonamide bond.

[5] The detection method according to [3] or [4], further including determining the degree of damage on the plasma membrane of a fluorescently imaged cell with reference to a fluorescence color tone of the cell upon detection of cancer cells in step (a-5).

[6] The detection method according to any one of [1] to [5], in which the method (b) comprises Papanicolaou staining.

[7] The detection method according to any one of [1] to [6], in which the plate has a thickness of 0.3 mm or less.

[8] The detection method according to any one of [2] to [7], in which the buffer-solution holding structure is a plate-like or ring-like structure having an opening corresponding to the buffer-solution holding region, and has a thickness sufficient to hold the buffer solution.

[9] The detection method according to [8], in which the buffer-solution holding structure is made of silicone, and has a thickness of 0.5 to 10 mm.

[10] The detection method according to any one of [1] to [9], in which the sample taken from the human includes cells originated from a cell suspension, exfoliative denuded cells, or fine-needle aspirated cells of a patient.

[11] The detection method according to [10], in which the cells are originated from a cell suspension selected from expectoration, urine, ascitic fluid, pleural fluid, pericardial fluid, cerebrospinal fluid, bile, pancreatic fluid, synovial fluid, or blood of a patient.

[12] The detection method according to [11], in which the cells are originated from an ascitic fluid of a patient having ovarian cancer or endometrial cancer.

[13] The detection method according to any one of [1] to [12], in which the plate has markings for showing positional information about the cells on a side opposite to a cell-attaching side.

[14] A glass or plastic plate structure for cell observation to observe living cells with a fluorescence microscope, including a glass or plastic plate for cell observation and a buffer-solution holding structure for holding a buffer solution, including:

a glass or plastic plate for attaching the cells thereon in a viable state, the plate having a buffer-solution holding region for holding a buffer solution to maintain the cells in a viable state on a surface, a thickness of 0.3 mm or less, and markings for showing positional information about the cells on a side opposite to a cell-attaching side, and a buffer-solution holding structure for holding the buffer solution in the buffer-solution holding region, the buffer-solution holding structure having a plate-like or ring-like shape, being configured to enclose the buffer-solution holding region, being made of silicone, and having a thickness of 0.5 to 10 mm.

Effects of the Invention

The present invention can provide a novel method of detecting cancer cells among living body-derived cells. Further, the present invention can provide a method for dual detection of cancer in which a method of detecting cancer cells by live imaging using a fluorescently labeled molecule is combined with an existing method of cytologically diagnosing cancer cells such as the Papanicolaou staining method and the Giemsa staining method.

BRIEF DESCRIPTION OF THE DRAWINGS

FIG. 1 shows an example of a glass plate and a buffer-solution holding structure dedicated for live-cell imaging, the glass plate being cut into the size of a glass slide used in the method according to the present invention. FIG. 1A shows a glass plate intended for live-cell imaging under an inverted microscope while maintaining suspended cells attached on a glass surface by centrifugation. The figure also shows an example where a silicone mask (buffer solution holding structure) having an opening is tightly fitted with the above glass plate. Printed marks for identifying cell positions are provided on the back side of the cell-attaching region of the glass plate to facilitate identification of cell positions. Further, the upper left portion of the glass plate is cut out to clarify the orientation of the glass plate. When actually used, a small amount (about 0.2 mL) of a buffer solution (a Krebs-Ringer solution, which hereinafter may be abbreviated as a KRB solution) is added to a rectangular water-repellent region drawn and formed on the glass plate with a commercially available PAP pen for immunohistochemistry so as to enclose the cell-attaching region to maintain the cells undried the completion of the subsequent attachment of a mask. The mask is made of silicone, and can be easily and tightly fitted with the glass plate without generating air bubbles, and can also be removed easily. The opening of the silicone mask is larger than the rectangular water-repellent region drawn and formed with a PAP pen, and about 1 mL of the KRB solution is instilled to the opening to perform microscopy. The mask has a stepped portion at the right end, and thus does not interfere with a projecting portion of a Keyence glass slide holder. FIG. 1B is an enlarged view of the printed portion (marking) provided on the back side of the glass plate which can be used for identifying cell positions. The size of the character is 0.5 mm×0.5 mm, and they are printed on the back side of the glass plate at a pitch of 2 mm in the length and width directions. The background texture represents a pattern of a paper underlying the glass plate in order to make a contrast against the transparent glass plate. FIG. 1C is a detailed view of the structure of the glass plate described above. FIG. 1D is a detailed view of the structure of a silicone mask serving as the buffer-solution holding structure described above.

FIG. 2 shows results from live-cell imaging of cells in peritoneal washing from a patient having ovarian cancer. FIG. 2A shows a bright-field image (the magnification at the objective lens was 100×) in which ascites cells obtained during an operation of a patient with ovarian cancer (serous adenocarcinoma) were subjected to microscopy while maintaining them in a viable state. FIG. 2B shows a fluorescence microscope image in the green wavelength region after applying a KRB solution containing 100 μM 2-NBDLG and 20 μM 2-TRLG. FIG. 2C is similar to FIG. 2B as described above except that it shows a fluorescence microscope image in the red wavelength region. FIG. 2D shows a superimposed image of the bright-field image and the fluorescence images.

FIG. 3 shows results from live-cell imaging of ascites cells obtained during an operation of a patient with endometrial cancer (endometrioid adenocarcinoma). FIG. 3A shows a bright-field image (the magnification at the objective lens is 40×) of two living-cell clusters which have been found to be suspected cancer cells from morphological observation. FIG. 3B shows a fluorescence microscope image in the green wavelength region after applying a KRB solution containing 100 μM 2-NBDLG and 20 μM 2-TRLG. FIG. 3C is similar to FIG. 3B as described above except that it shows a fluorescence microscope image in the red wavelength region. FIG. 3D shows an enlarged bright-field image (the magnification at the objective lens is 100×) of the cell cluster (Cluster 1) at the right side of the view in FIG. 3C.

FIG. 4 shows results from correspondence of the results from live-cell imaging of the ascites cells obtained during an operation of a patient with endometrial cancer (endometrioid adenocarcinoma) with the results from the subsequent Papanicolaou staining. FIG. 4A shows an enlarged fluorescence microscope image in the green wavelength region of the cell cluster (Cluster 1) at the right side of the view in FIG. 3B. FIG. 4B shows an enlarged fluorescence microscope image in the red wavelength region of the cell cluster (Cluster 1) at the right side of the view in FIG. 3C. FIG. 4C shows a superimposed image of the bright-field image and fluorescence images of the cell cluster (Cluster 1) in FIG. 3D, FIG. 4A, and FIG. 4B. FIG. 4D shows a bright-field image of the cell cluster (Cluster 1) shown in FIG. 3D, FIG. 4A, and FIG. 4B, i.e., a cell cluster positive for 2-NBDLG but negative for 2-TRLG, after subjected to Papanicolaou staining.

FIG. 5A shows a fluorescence microscope image (the magnification at the objective lens is 40×) in the green wavelength region after applying a KRB solution containing 100 μM 2-NBDLG and 20 μM 2-TRLG. FIG. 5B is similar to FIG. 5A as described above except that it shows a fluorescence microscope image in the red wavelength region. FIG. 5C shows a superimposed image of a bright-field image and the fluorescence images of FIGS. 5A and 5B. FIG. 5D shows results from Papanicolaou staining performed after fluorescent staining.

FIG. 6A shows a superimposed image of the fluorescence microscope image (the magnification at the objective lens is 40×) in the green wavelength region, the fluorescence microscope image in the red wavelength region, and the bright-field image in the entire cell-attaching region before application of a KRB solution containing 100 μM 2-NBDLG and 20 μM 2-TRLG. FIG. 6B shows a superimposed image of the fluorescence microscope image (the magnification at the objective lens is 40×) in the green wavelength region, the fluorescence microscope image in the red wavelength region, and the bright-field image after application of a KRB solution containing 100 μM 2-NBDLG and 20 μM 2-TRLG.

FIG. 7A shows the fluorescence microscope (the magnification at the objective lens is 40×) in the green wavelength region before application of a KRB solution containing 100 μM 2-NBDLG and 20 μM 2-TRLG, and FIG. 7C shows a superimposed image of FIG. 7A and a bright-field image. FIG. 7B shows the fluorescence microscope in the green wavelength region after application of a KRB solution containing 100 μM 2-NBDLG and 20 μM 2-TRLG, and FIG. 7D shows a superimposed image of FIG. 7B and a bright-field image.

FIG. 8A shows a fluorescence microscope image at the green wavelength region, and FIG. 8B shows a fluorescence microscope image at the red wavelength region. FIG. 8C shows a superimposed image of FIG. 8A, FIG. 8B, and a bright-field image. FIG. 8D shows a bright-field image of the cell cluster shown in FIGS. 8A and 8B, i.e., a cell cluster positive for 2-NBDLG but negative for 2-TRLG, after performing Papanicolaou staining.

FIG. 10A shows a superimposed image of the fluorescence microscope image in the green wavelength region, the fluorescence microscope image in the red wavelength region, and the bright-field image in the entire cell-attaching region before application of a KRB solution containing 100 μM 2-NBDLG and 20 μM 2-TRLG. FIG. 10B shows a superimposed image of the fluorescence microscope image (the magnification at the objective lens is 40×) in the green wavelength region, the fluorescence microscope image in the red wavelength region, and the bright-field image after application of a KRB solution containing 100 μM 2-NBDLG and 20 μM 2-TRLG.

FIG. 11A shows the fluorescence microscope image (the magnification at the objective lens is 40×) in the green wavelength region before application of a KRB solution containing 100 μM 2-NBDLG and 20 μM 2-TRLG, and FIG. 11C shows a superimposed image of FIG. 10A and a bright-field image. FIG. 11B shows the fluorescence microscope image in the green wavelength region after application of a KRB solution containing 100 μM 2-NBDLG and 20 μM 2-TRLG, and FIG. 11D shows a superimposed image of FIG. 10B and the bright-field image.

FIG. 12A shows a fluorescence microscope image in the green wavelength region, and FIG. 12B shows a fluorescence microscope image in the red wavelength region. FIG. 12C shows a superimposed image of FIG. 12A, FIG. 12B, and a bright-field image. FIG. 12D shows a bright-field image of the cell clusters (a, b) shown in FIG. 12A and FIG. 12B, i.e., cell clusters negative for 2-NBDLG and negative for 2-TRLG, after subjected to Papanicolaou staining.

PREFERRED MODE FOR CARRYING OUT THE INVENTION

Figure 5:
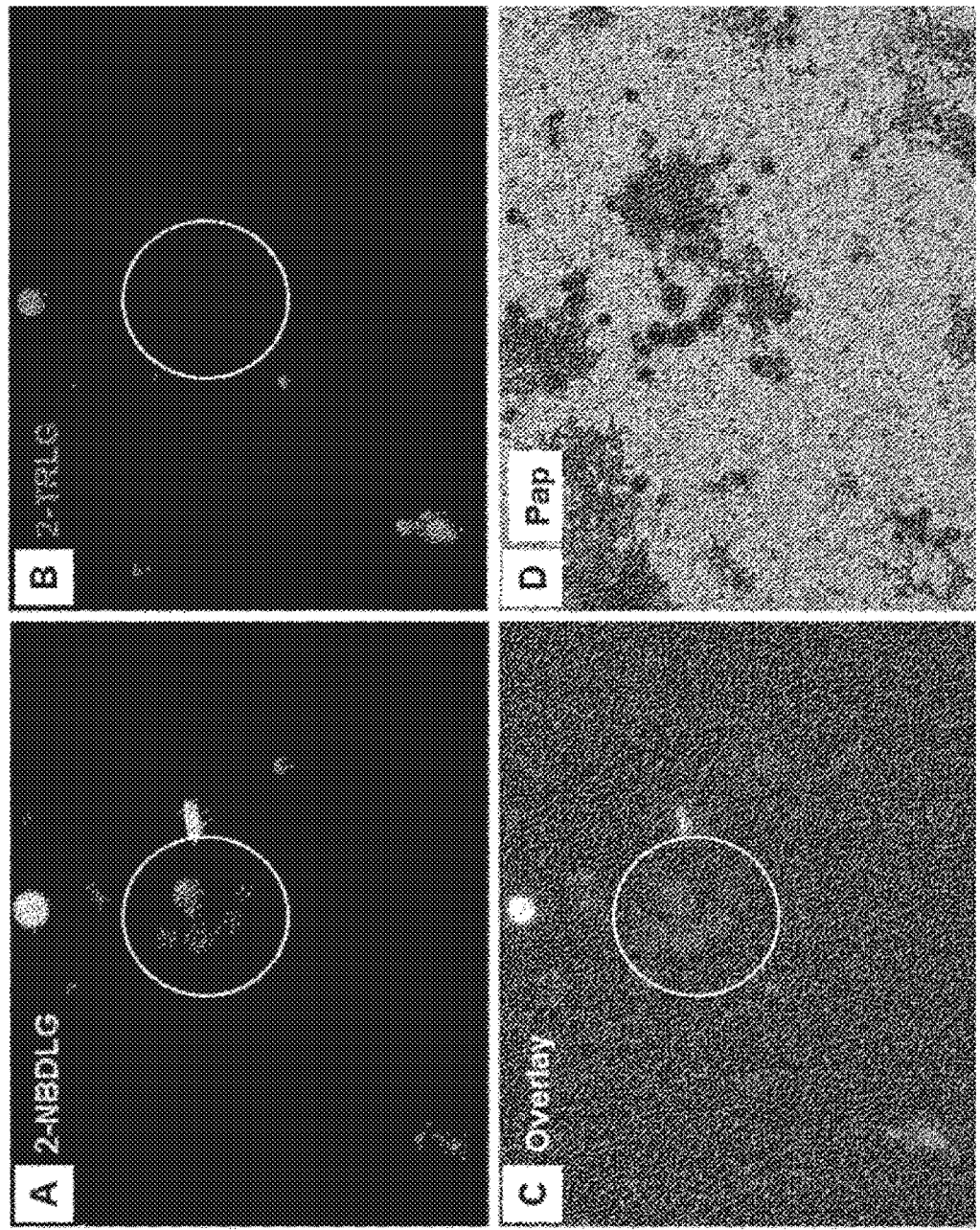
FIG. 5 shows results from correspondence of the results from live-cell imaging of the ascites cells obtained during an operation of a patient with endometrial cancer (endometrioid adenocarcinoma) with the results from the subsequent Papanicolaou staining.
Figure 6:
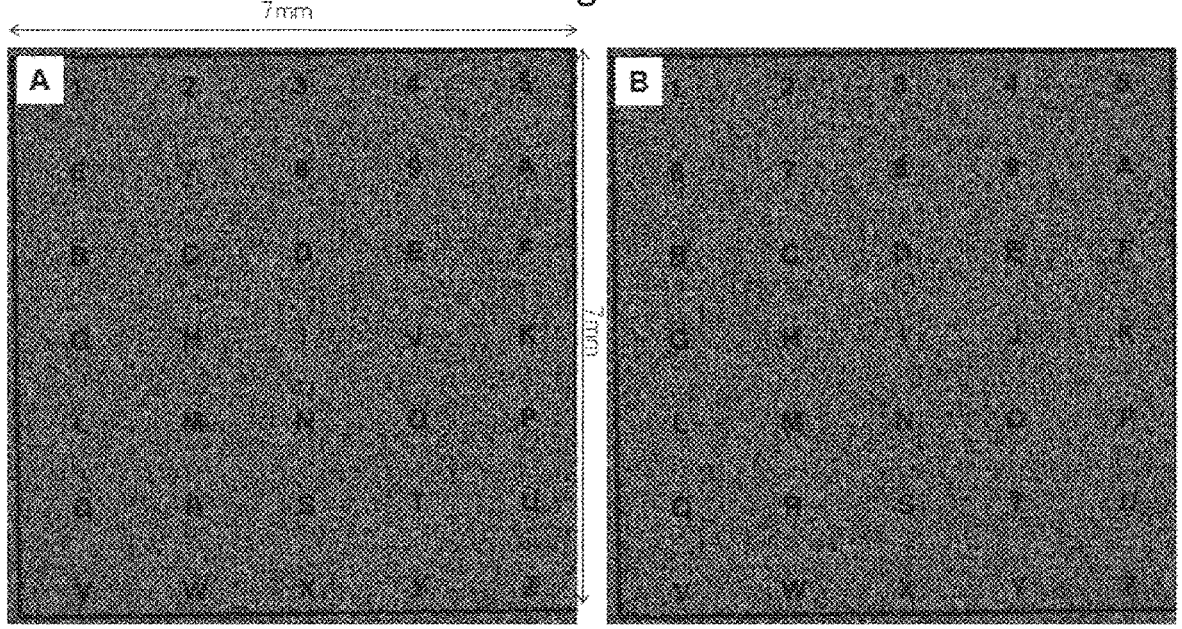
FIG. 6 shows results from the entire-field live-cell imaging of the ascites cells obtained during an operation of a patient with ovarian cancer (serous adenocarcinoma) in the cell-attaching region.
Figure 7:
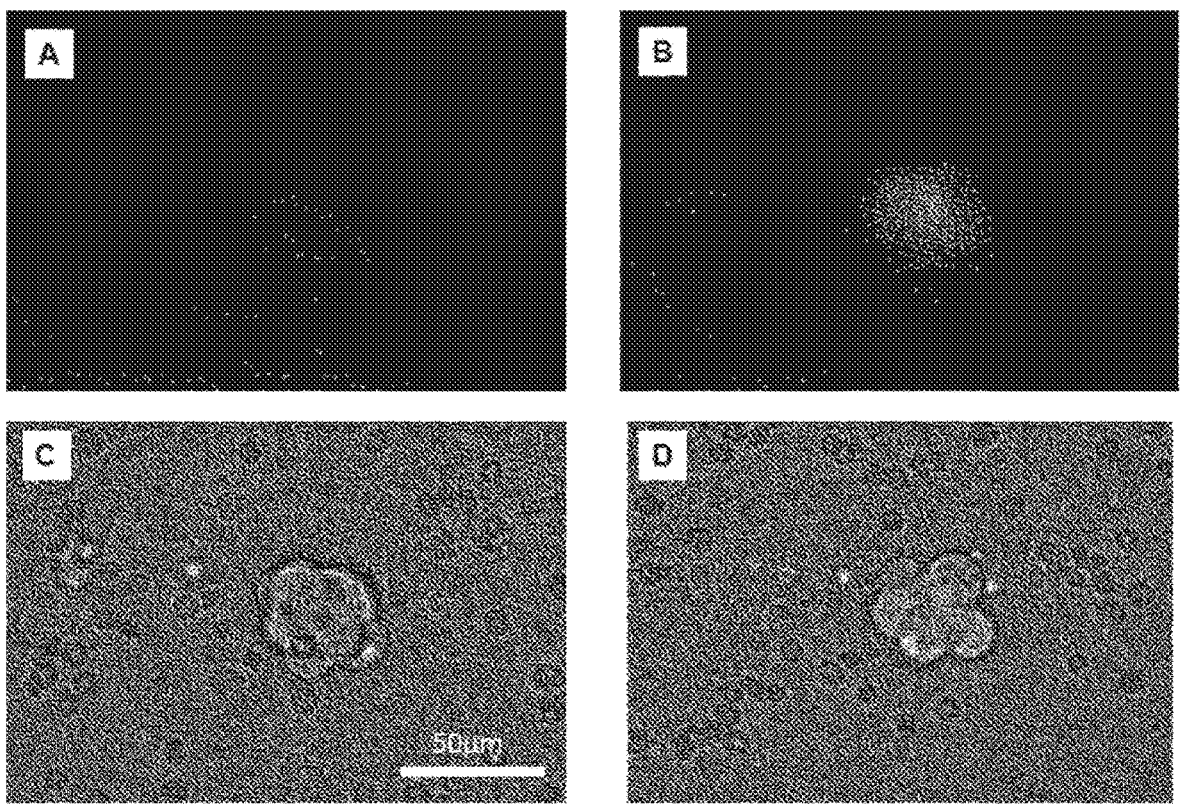
FIG. 7 shows results from live-cell imaging of the ascites cells obtained during an operation of a patient with ovarian cancer (serous adenocarcinoma).
Figure 8:
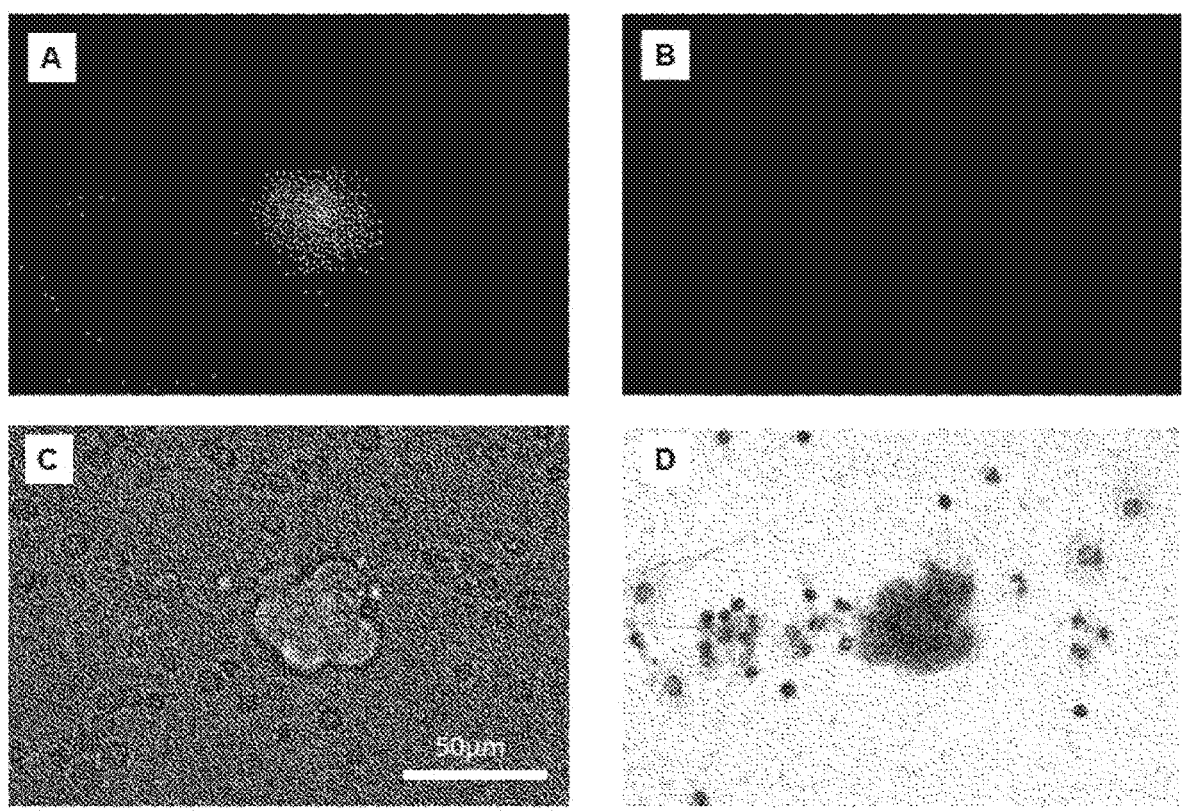
FIG. 8 shows results from correspondence of the results from live-cell imaging of the ascites cells obtained during an operation of a patient with ovarian cancer (serous adenocarcinoma) with the results from the subsequent Papanicolaou staining.
Figure 9:
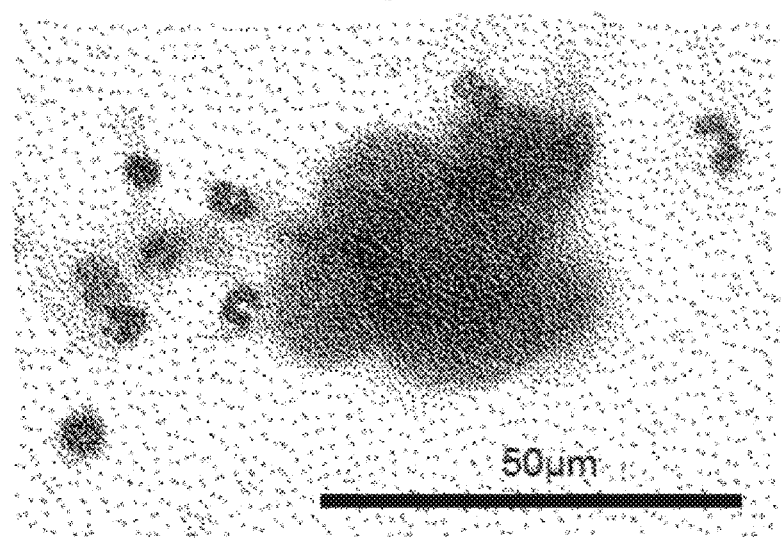
FIG. 9 shows an enlarged view of the Papanicolaou staining in FIG. 8D.
Figure 10:
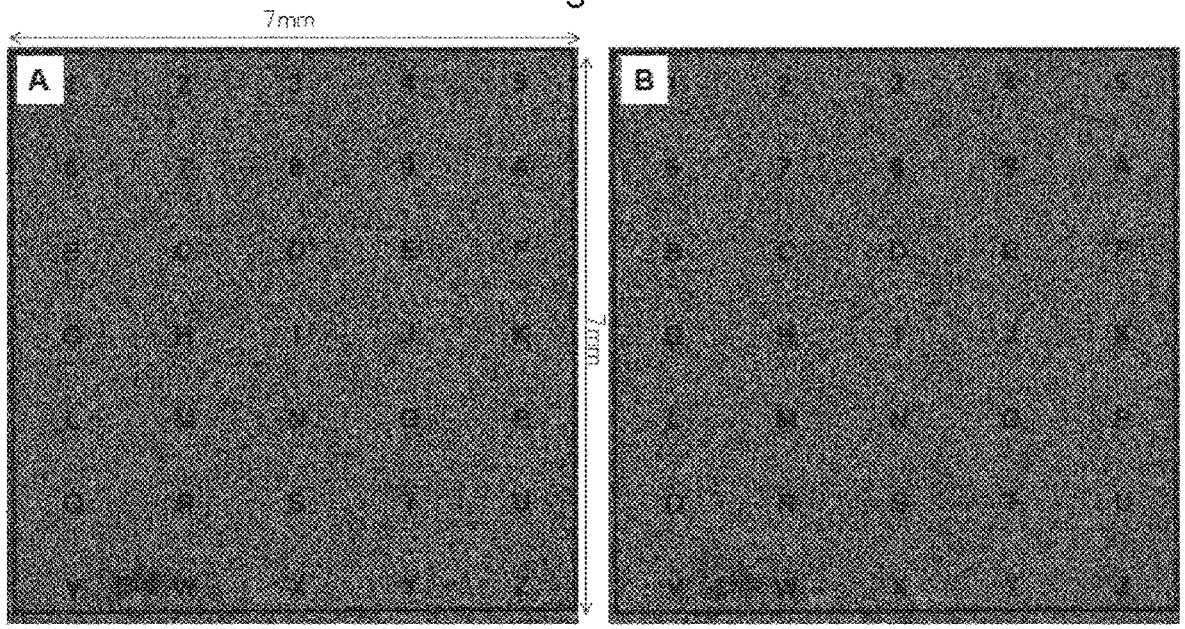
FIG. 10 shows results from the entire-field live-cell imaging of the cells in peritoneal washing obtained during an operation of a patient with endometrial cancer (endometrial endometrioid adenocarcinoma) in the cell-attaching region.
Figure 11:
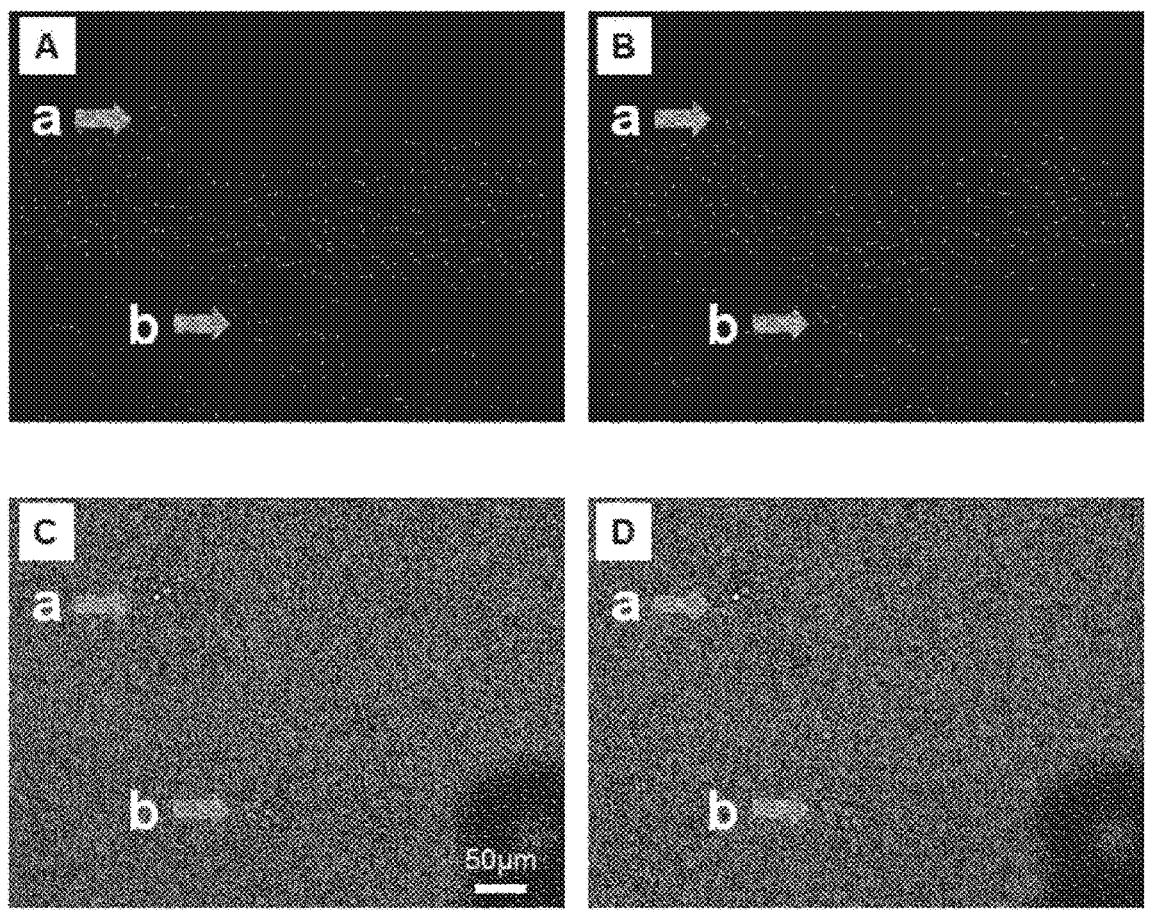
FIG. 11 shows results from live-cell imaging of the cells in peritoneal washing obtained during an operation of a patient with endometrial cancer (endometrial endometrioid adenocarcinoma).
Figure 12:
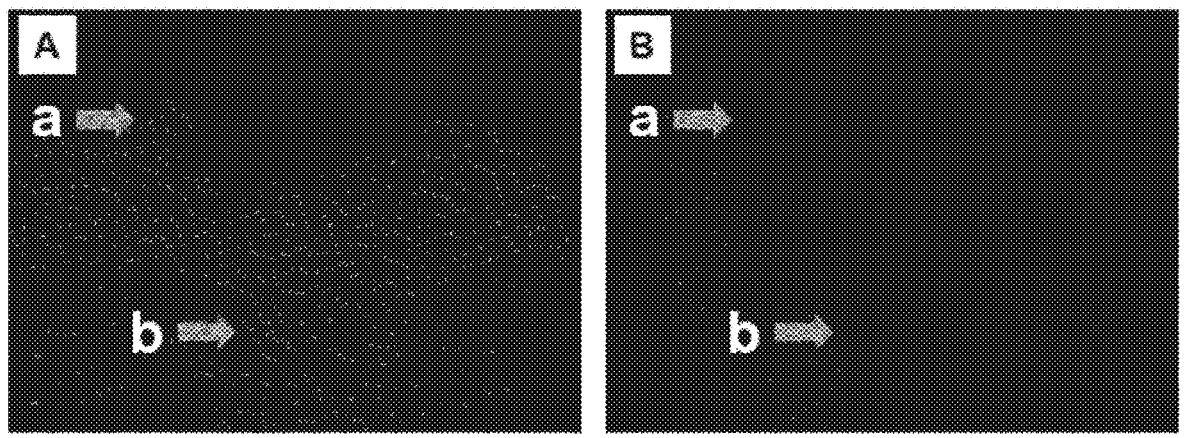
FIG. 12 shows results from correspondence of the results from live-cell imaging of the cells in peritoneal washing obtained during an operation of a patient with endometrial cancer (endometrial endometrioid adenocarcinoma) with the results from the subsequent Papanicolaou staining.
Figure 13:
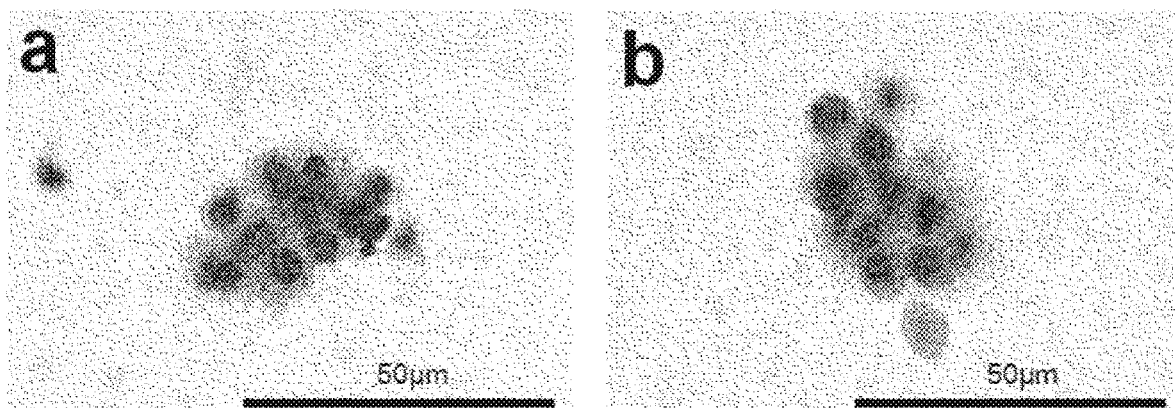
FIG. 13 shows an enlarged view of the Papanicolaou staining in FIG. 12D.

One aspect of the present invention relates to a method of detecting cancer cells among living body-derived cells, the method including: allowing for intracellular uptake of a specific fluorescently labeled molecule, and detecting fluorescence from the specific fluorescently labeled molecule uptaken intracellularly while maintaining the cells in a viable state. This can be achieved by allowing the cells to attach and remain on a thin glass or plastic plate, and providing a buffer-solution holding region for holding a buffer solution on the plate. One aspect of the method of detecting cancer cells according to the present invention can provide a method of detecting cancer including fluorescence imaging of living cells (step (a)) as described below. A method of detecting cancer cells including:

(i) incubating the cells with a fluorescently labeled L-glucose derivative, the L-glucose derivative having a 7-nitrobenz-2-oxa-1,3-diazole group or a derivative thereof as a fluorophore on the molecule thereof, and detecting the intracellularly uptaken fluorescently labeled L-glucose derivative, and (ii) detecting fluorescence from the L-glucose derivative present inside a cell while allowing the cells to attach on a thin glass or plastic plate, the plate having a region for holding a buffer solution to maintain the cells in a viable state on a surface thereof, and the detection of fluorescence from the L-glucose derivative present inside the cell being indicative of the cell being cancerous.

One aspect of the method of detecting cancer cells according to the present invention can provide a method for dual detection of cancer cells, including step (a) described above as well as a method of staining a cell fixed with a fixing solution such as alcohol or formalin as described below (a step (b)).

(b) A method of detecting cancer cells, including immersing the plate into an ethanol fixing liquid to fix the cells, and then performing staining by any one method selected from the group consisting of Papanicolaou staining, Giemsa staining, PAS staining, Grocott staining, and immunocytochemical staining.

An L-glucose derivative having 7-nitrobenz-2-oxa-1,3-diazole group or a derivative thereof on the molecule thereof as a fluorophore which can be used in step a described above is specifically disclosed in WO2010/016587 and WO2012/133688 which belong to the present inventors. Examples of the L-glucose derivative include, for example, but not limited to, 2-[N-(7-nitrobenz-2-oxa-1,3-diazole-4-yl)amino]-2-deoxy-L-glucose (2-NBDLG), 4-deoxy-4-[N-(7-nitrobenz-2-oxa-1,3-diazole-4-yl)amino]-L-glucose (4-NBDLG), 6-deoxy-[N-(7-nitrobenz-2-oxa-1,3-diazole-4-yl)amino]-L-glucose (6-NBDLG), 2-deoxy-2-[N-7-(N',N'-dimethylaminosulfonyl)benz-2-oxa-1,3-diazole-4-yl)amino]-L-glucose (2-DBDLG), and the like. A particularly preferred L-glucose derivative is 2-NBDLG.

The incubation temperature in step (a) is 22 to 37.5° C., preferably 36 to 37.5° C., and more preferably about 37° C. Here, about 37° C. is meant to be 36.6° C. to 37.5° C., The incubation duration in step (a) may be appropriately selected according to the conditions of cells, the type of the fluorescently labeled L-glucose derivative to be used, or the detection conditions, but it is usually 15 minutes or less, preferably 3 to 15 minutes, and more preferably 3 to 5 minutes.

As art approach for stopping uptake of an L-glucose derivative in step (a), a method in which an specific uptake of the L-glucose derivative by the cells can be stopped while the cells can be maintained in a viable state can be selected. Examples of the approach can include, for example, (i) placing the cells under a low temperature condition, (ii) replacing with a buffer solution free from the L-glucose derivative, (iii) adding an agent which can inhibit uptake of the L-glucose derivative. Examples of (i) can include, for example, placing cells in a buffer solution cooled at 0° C. As for (ii), washing with a buffer solution free from the L-glucose derivative (a free buffer solution) is preferably performed when replacing the buffer with the free buffer solution. Alternatively, replacing may be performed by perfusion of the free buffer solution. Examples of (iii) can include, for example, adding a water-channel inhibitor serving as a 2-NBDLG uptake inhibitor such as phloretin to a cell solution.

The present invention can be characterized by performing fluorescence observation under conditions where cells are attached and maintained in a viable state. Further, the present invention can also be characterized by using a thin glass or plastic plate structure (hereinafter, may simply be referred to as a "glass or plastic plate," a "glass plate," a "plastic plate," or a "plate") having a region (buffer-solution holding region) for holding a buffer solution to maintain cells in a viable state on a surface thereof as a support for allowing the cells to attach thereon to perform fluorescence observation.

There is no particular limitation for the glass plate which can be used in the present invention as long as fluorescence from cells can be detected with a fluorescence microscope and the like, and known glass plates, such as a thin glass plate (for example, a cover glass) adapted for use in the present invention may be used A plastics plate which can be used in the present invention may be made of a non-fluorescent or low-fluorescent material in order to detect fluorescence from cells with a fluorescence microscope and the like. Plates can include, but not limited to, for example, low-autofluorescent plastic cover slips such as CrystalClene (Molecular Dimensions), Correlative Microscopy Coverslips (Electron Microscopy Sciences), and Cell Desk LF (Sumitomo Bakelite Co., Ltd.). A glass or plastic plate which can be used in the present invention needs to be thin in order to detect fluorescence from an individual cell with a fluorescence microscope and the like. Examples of the thickness include, for example, 0.3 mm or less, preferably 0.2 mm or less, and particularly preferably 0.12 to 0.20 mm. These correspond to glass thicknesses of common cover glasses for covering glass slides upon cell observation. As used in the present specification, a thin glass plate for use in the present invention may be referred to as a cover glass dedicated for live-cell imaging, or may be simply referred to as a glass plate.

It is noted that the thickness of a glass or plastic plate may be 1 mm for the purpose of detecting fluorescence from cells instead of performing detailed fluorescence imaging of cells (morphology and the like).

The region for holding a buffer solution to maintain cells in a viable state on a surface of a glass or plastic plate (hereinafter, may be referred to as the "buffer-solution holding region") is configured to be able to hold a buffer solution on the plate so that the buffer solution does not easily flow out when the plate is inclined. There is no particular limitation for the shape of the above region, and, for example, rectangular shapes, circular shapes, elliptic shapes, fish-like shapes, and the like can be used Examples of the above plate can include, but not limited to, a glass or plastic plate having a water-repellent region created or printed on the plate so as to enclose a buffer-solution holding region, or a glass or plastic plate having a structure for preventing outflow of a liquid (preferably, a structure made of a water-repellent material, such as silicone) provided on the plate so as to enclose a buffer-solution holding region. Examples of the former can include, but not limited to, a glass or plastic plate on which a water-repellent ink is printed so as to enclose a buffer-solution holding region. A structure of the latter may be pre-arranged on a glass or plastic plate, or may be arranged after allowing cells to attach on a glass or plastic plate, or may even be integrated with a glass or plastic plate.

It is noted that the buffer-solution holding region may be configured so as to include and enclose a cell-attaching region on which cells are allowed to attach. The buffer-solution holding region may be almost as large as the cell-attaching region, or may be larger by several times or more as compared with the cell-attaching region. However, in order to maintain cells in a sufficient amount of a buffer solution, the buffer-solution holding region should be larger than the cell-attaching region preferably by 2 times or more, and more preferably 5 times or more, but preferably 10 times or less.

The glass or plastic plate used in the present invention may have markings for providing positional information about cells on a side opposite to a cell-attaching side. It is desirable that the marks, symbols, letters, lines and the like serving as the above markings have sizes, shapes, and optical properties which do not interfere with visible-light or fluorescence observation of cells, and that they are, if possible, resistant against aqueous solutions, organic solvents, and friction, so as not to disappear easily. When letter patterns of an ink are firmly applied by heat using a technique such as silk screening, small letters can be read, and will also be resistant against water and organic solvents described above. For a glass plate, markings may be formed by notching with a diamond knife or by creating grooves and depressed portions on the back side or the inside of the glass plate using a pulsed laser and the like at an appropriate intensity. These can facilitate observation of cells, and also enables identification of cells in the dual detection method according to one aspect of the present invention described below.

Further, in the detection method according to the present invention, sufficient retention of a buffer solution in a buffer-solution holding region of a glass or plastic plate can be achieved by virtue of a buffer-solution holding structure (in the present specification, may also be referred to a "mask") configured to enclose the buffer-solution holding region. Examples of the shape of the above mask can include a plate-like or ring-like shape having an opening corresponding to the aforementioned region. A plate-like shape is preferred. There is no particular limitation for the thickness of a mask as long as the above objectives can be achieved. There is no particular limitation for the material of a mask as long as it can be tightly fitted with a surface of a glass or plastic plate without generating air bubbles. Further, it is preferably non-fluorescent.

Examples of the thickness of a mask can include, but not limited to, 0.5 to 10 mm, preferably 1 to 5 mm, more preferably 2 to 5 mm, and even more preferably 2 to 3 mm. Examples of the material of a mask can include, but not limited to, a resin such as silicone, a metal on which a coating is applied in order to increase adhesion to a plate. Further, the opening of the mask is preferably configured so that the mask does not make contact with the cell-attaching region in the course of the mask being tightly fitted with the glass, and that the mask can be easily attached and removed. For example, a silicone resin with a thickness of 2 mm formed as shown in FIG. 1 or 14 may be used, and a projecting portion for handling may be provided to facilitate attachment and removal.

Figure 14:
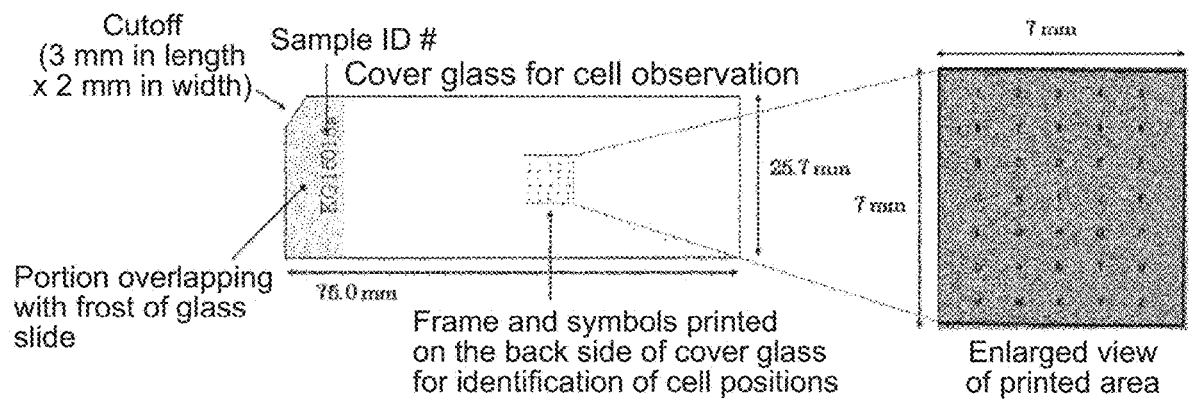
FIG. 14 shows a cover glass for cell observation. Printed marks for identifying cell positions are provided on the back side of a 7 mm×7 mm cell-attaching region at the center to facilitate identification of cell positions. Further, the upper left portion of the glass plate is cut out to clarify the orientation of the glass plate. When actually used, a rectangular water-repellent region is drawn and formed on the glass plate with a commercially available PAP pen for immunohistochemistry so as to enclose the cell-attaching region. This can prevent an outflow of a buffer solution (a Krebs-Ringer solution, which hereinafter may be abbreviated as a KRB solution and proves to be effective in retaining liquid volume.

As shown in FIG. 1 or 14, the shape of a mask may be designed so as to be unsymmetrical in terms of the vertical and horizontal directions, and to be able to fit on a glass plate so that an end of the mask coincides with an edge of the glass plate.

This can ensure that the opening is always placed at the same position, eliminating a risk of misplacing the mask over cells. With reference to FIG. 1, the cell-attaching region has the substantially the same size as the buffer-solution holding region, and the opening of the mask also has substantially the same size as the cell-attaching region. With reference to FIG. 14, the buffer-solution holding region is larger (by about 5 times) than the cell-attaching region, and the opening of the mask (the opening of the outer mask) corresponding to the buffer-solution holding region is also larger than the cell-attaching region. In the example shown in FIG. 14, the opening of the inner mask has substantially the same size as the cell-attaching region.

A mask (a buffer-solution holding structure) for use in perfusion may be asymmetrical in terms of the vertical and horizontal directions for easy identification of the orientation, and sized so as not to hide the sample name and the like shown on the glass plate, and configured so as to be easily and tightly fitted on the glass plate without generating air bubbles, and easily removed without affecting cells. The present mask has a nested structure, and includes (i) an inner mask having an opening of the same size as the cell-attaching region, and (ii) an outer mask having an opening configured such that the inner mask can be fit therein, and that it creates a gap for the easy removal of the inner mask.

(i) The opening of the inner mask is configured to include and enclose the cell-attaching region, and may be pre-combined with the outer mask to be tightly fitted with a glass or plastic plate. This can prevent cells from flowing out of the cell-attaching region upon centrifugation. When the inner mask is removed after centrifugation, the buffer solution retained at the opening of the inner mask may flow out of the cell-attaching region, resulting in dehydration of cells. Therefore, a water-repellent enclosure is preferably provided at or outside the outer periphery of the cell-attaching region.

(ii) The opening of the outer mask includes and encloses the cell-attaching region and the water-repellent enclosure. When perfusion with a KRB solution is started in a state where the inner mask is removed after cell adhesion and a cover glass which is sized not to block the opening is attached, the outer mask may have a shape such that the KRB solution flowing from the Inlet can flow into the Outlet side, and the excess solution does not spill over to the Inlet side, but to the Outlet side (hereinafter may be referred to as a "fish-like opening").

Further, an appropriate jig for helping the mask to be tightly fitted with a glass plate in a certain positional relationship to each other may be effective for correctly attaching the present mask on the glass plate. The shape of the mask is preferably designed so that, when a permanent preparation is prepared using a glass slide, the mask does not make contact with the frost portion, and the date, sample name, and the like are not obscured or can be easily read. This may be achieved by providing a mask having a slightly smaller size so as not to hide the sample-name area as shown in the example in FIG. 1. However, when the silicone mask described above is used, letters under the silicone mask can be easily read. Therefore, a smaller mask may not necessarily be required. Such a structure may be configured so as to enclose the aforementioned buffer-solution holding region to prevent outflow of the liquid. In that case, a glass plate having such a structure thereon corresponds to a glass plate having a region for holding a buffer solution to maintain cells in a viable state on a surface thereof according to the present invention.

In step a, cells will attach on a cell-attaching region (such as a region inside the hydrophobic region in FIG. 1) located approximately at the center of a glass plate. Adhesion of cells on the glass plate in step (a) may be achieved by, without limitation, centrifugation. Centrifuge conditions can be appropriately selected. For example, a centrifugal force causing less damage to cells may be used at room temperature. Further, the method according to the present invention can be used in combination with an automated cell collecting system (an automated smearing system and the like), with which cells can easily be collected to attach on a glass plate.

Another aspect of the present invention can provide the above method of detecting cancer cells in which the fluorescently labeled L-glucose derivative is a mixture of an L-glucose derivative having a 7-nitrobenz-2-oxa-1,3-diazole group or a derivative thereof on the molecule thereof as a fluorophore and 2-amino-2-deoxy L-glucose (2-TRLG) in which a sulforhodamine 101 is attached at position z via a sulfonamide bond.

A fluorescently labeled glucose derivative may non-specifically enter the inside of cells with damaged plasma membrane, regardless of whether the cells are cancer cells or non-cancer cells (including normal cells). Use of the mixture of the fluorescently labeled L-glucose derivatives as described above can distinguish non-specific uptake of the fluorescently labeled glucose derivatives into non-cancer cells with damaged plasma membranes from uptake into cancer cells.

Ascites cells or cells in urine are exposed to an environment considered as intrinsically hostile to cell viability, and thus many of them are in a state somewhere between fully viable cells and completely dead cells. Some of these cells show increased plasma-membrane permeability, but are not dead. Accurate knowledge about the conditions of these cells can provide important information for detecting cancer cells.

Use of 2-TRLG, a derivative having both a fluorophore with intermediate steric bulk and moderate lipophilicity, and L-glucose which is water soluble and does not bind to GLUT in the molecule thereof enables various cell conditions to be determined and distinguished. In contrast, when known molecules, such as propidium iodide and DAPI which enter the inside of a cell through a damaged portion in the plasma membrane to irreversibly bind to the nucleus, and a molecule in which a fluorophore is attached to simply bulky dextran or the like are used, differences in cell conditions cannot be accurately detected. That is, simultaneously applying to cancer cells a fluorescent L-glucose derivative 2-TRLG on which a large red fluorophore Texas Red is attached and 2-NBDLG on which a green fluorophore NBD is attached can distinguish differences in how cells uptake the fluorescent L-glucose derivatives based on a continuous spectrum of fluorescence color from green to red. This is a unique feature not found in cytodiagnosis techniques based on the conventional fluorescent molecular probes.

Further, detection of fluorescence in the method of detecting cancer cells according to the present invention can be performed in accordance with a known method. Further, detection of cells according to the present invention can be performed by directly observing fluorescence, or converting fluorescence into DAB or the like by the photoconversion method, and then performing observation under a light microscope or an electron microscope. By appropriately selecting a reference value, the degree of anomalies in cell functions can be shown not only qualitatively but also quantitatively or automatically.

There is no particular limitation for living body-derived cells targeted in the method of detecting cancer cells according to the present invention as long as they are cells from a patient suspected of cancer. They can include, but not limited to, for example, cells originated from a cell suspension, exfoliative denuded cells, or fine-needle aspirated cells of a patient. Cells originated from a cell suspension are preferred.

A cell suspension can be obtained from, without limitation, expectoration, urine, ascitic fluid, pleural fluid, pericardial fluid, cerebrospinal fluid, bile, pancreatic fluid, synovial fluid, or blood of a patient.

Exfoliative denuded cells can include, but not limited to, for example, exfoliative cells taken by scratching the cervix of the uterus, the uterine body, the vaginal wall, the vulva, or the surface of bronchus under the bronchoscope with a cotton swab or a brush. Fine-needle aspirated cells can include, but not limited to, for example, cells aspirated through a needle inserted into tumors found in thyroids, mammary glands, salivary glands, liver, subcutaneous tissues, lymph nodes, and the like. Moreover, there is no particular limitation for the types of cancer targeted in the method of detecting cancer cells according to the present invention as long as cells can be sampled. They can include, for example, gynecologic cancer such as ovarian cancer, endometrial cancer, and cervical cancer; digestive system cancer such as stomach cancer, colon cancer, biliary tract cancer, pancreatic cancer, and esophagus cancer; respiratory system cancer such as lung cancer; thyroid cancer; breast cancer; urinary system cancer such as bladder cancer, renal pelvic cancer, ureter cancer, and prostatic cancer; hematopoietic malignancy such as leukemia and malignant lymphoma; and cerebrospinal fluid cancer such as malignant tumors which have invaded the central nervous system. Suspended cells from an ascitic fluid can include, for example, cells from an ascitic fluid of a patient with ovarian cancer, endometrial cancer, stomach cancer, colon cancer, biliary tract cancer, pancreatic cancer, or esophagus cancer. In addition, examples in which suspended cells from a pleural fluid are used can include respiratory system cancer such as lung cancer; thyroid cancer; and breast cancer. Examples in which cells from urine are used can include urinary system cancer such as bladder cancer, renal pelvic cancer, ureter cancer, prostatic cancer, and the like. Examples in which blood cells are used can include hematopoietic malignancy such as leukemia and malignant lymphoma. Examples in which cells from exfoliative denuded cells can include cervical cancer, endometrium cancer, oral cancer, and the like. Examples in which cells from fine-needle aspirated cells are used can include mammary gland cancer and thyroid cancer.

There is no particular limitation for the buffer solutions which can be used in the method of detecting cancer cells according to the present invention as long as they can appropriately maintain living-body derived cells in a viable state. They can include, but not limited to, for example, KRB solutions, culture media (such as Dulbecco's modified Eagle medium supplemented with fetal bovine serum), organ preservation solutions (Saviosol, UW preservation liquid), and the like.

Below, a series of steps in the detection method according to the present invention will be described with reference to a dual detection method including live-cell imaging with the fluorescently labeled L-glucose derivative according to the present invention and Papanicolaou staining. However, the present invention shall not be limited to this, and various modifications may be made using known technologies and the like without departing from the spirit and scope of the present invention.

A cell sample taken from a living body is suspended in an appropriate buffer solution such as the Ca—Mg-free Hanks solution in which clots are not easily formed, and transported to a laboratory. When test procedures cannot be started immediately, the cell sample may be stored in a cool and dark place at room temperature. On the next day after acquisition of the cell sample, a fluorescently labeled L-glucose derivative may be applied to perform observation. Further, when a large amount of hemocytes are contained, a portion above the pellet (commonly called as a buffy coat) may be collected, and be subjected to hemolysis operations commonly performed for cytological sample pretreatment or clot removal operations.

Below, aspects of the present invention will be described in which cells are treated with 2-NBDLG and 2-TRLG, and allowed to attach on a glass plate, and then observed for fluorescence, thereby detecting cancer. A cell-containing sediment is separated from a supernatant by centrifugation.

Any centrifuge conditions commonly used in laboratory can be used, but short and minimal centrifugation is preferred in view of maintaining the cells in a viable state. For example, centrifugation may be performed once or twice at 650 G to 1500 G for 1 minute to 2 minutes. A small amount of a KRB solution is added to the pellet, and the pellet is then dispersed. The subsequent staining operation may be immediately started, or alternatively a large amount of a buffer solution may be added and stored for up to 24 hours until the staining operation. In the case of the latter, centrifugation is again performed before the staining operation.

2-NBDLG and 2-TRLG are mixed and dissolved in a KRB solution to give a concentration twice as high as the final concentration, and warmed at 37 degrees for future use (the ×2 fLG solution). Here, an inhibitor may be added to the KRB solution, depending on purposes. For example, without limitation, carbenoxolone, a gap junction inhibitor, is preferably added to block uptake of 2-NBDLG through the gap junction/hemichannel. The cell-containing KRB solution is mixed with an equal amount of the fLG solution pre-prepared as described above to expose the cells to fLG for a certain period of time, allow for intracellular uptake of fLG. Contact time, temperature conditions, and the like can be found in publicly known literatures (see WO2012/133688). A large excess of a cold KRB solution (0° C.) is added to stop the uptake of fLG, and fLG in the solution is removed by centrifugation at 0° C. This process may be repeated, if desired, until the concentration of fLG in the solution is sufficiently decreased. Use of the cold KRB solution enables a highly reproducible uptake process of fLG.

The cells are allowed to be suspended in an adequate amount of the cold KRB solution, and to attach on a surface of the aforementioned glass or plastic plate by centrifugation. The above centrifuge process can be achieved relatively easily when a commercially available automated cell collecting system with a cell centrifugation capability is used Centrifugation is preferably performed for a short time to prevent dehydration of cells (1 to 2 minutes), and a small amount of the KRB solution is added to a cell-attaching region immediately after centrifugation.

Below, aspects of the present invention will be described in which cells are allowed to attach on a glass plate, and then treated with 2-NBDLG and 2-TRLG, and observed for intracellularly uptaken fluorescence to detect cancer. A large amount of hemocytes may be contained in a cell sample transported in the form of a suspension in a buffer solution, but cells of interest can be effectively collected while maintaining the cells in a viable state without performing hemolysis procedures when a dual centrifugation method is used First, centrifugation is performed once at a speed where the majority of red blood cells are spinned down, but the cells of interest are not, such as at 200 G to 400 G for 1 to 3 minutes, and the supernatant containing the cells of interest is completely recovered. Next, the recovered supernatant is centrifuged once at a speed where all cells are spinned down, such as at 500 G to 650 G for 1 to 3 minutes, and 1 to 2 mL of a portion above the pellet are taken, the portion containing a large amount of red blood cells. The next operation may be started immediately, or alternatively a large amount of a buffer solution may be added and stored for up to about 24 hours. In the case of the latter, centrifugation is again performed once at 650 G to 1500 G for 1 minute to 2 minutes before operations.

2-NBDLG and 2-TRLG are mixed and dissolved in a KRB solution to give the final concentration, and warmed at 37 degrees for future use (fLG solution). Here, an inhibitor may be added to the KRB solution, depending on purposes. For example, without limitation, carbenoxolone, a gap junction inhibitor, is preferably added to block uptake of 2-NB-DLG through the gap junction/hemichannel.

The fLG solution pre-prepared as described above is allowed to flow by performing perfusion at a rate of 0.3 mL/min to 1.4 mL/min, and cells are exposed to fLG for a certain period of time to allow for intracellular uptake of fLG. Contact time, temperature conditions, and the like can be found in publicly known literatures (see WO2012/133688). Perfusion is switched from the fLG solution to the KRB solution to stop the uptake of fLG, removing fLG in the solution. Perfusion performed for 5 minutes to 15 minutes until the concentration of fLG in the solution is sufficiently decreased, and then fluorescence from cells after application can be observed. Tiling image acquisition, in which the entire cell-attaching region is sequentially imaged per view, and then combined together after observation, may be performed instead of individually acquiring images of the cells of interest. This enables retrospective review of the entire region to prevent missed cells of interest. Further, intrinsic fluorescence from the cells can be observed before application of the fLG solution by perfusion. This enables more accurate determination whether or not the fluorescently labeled L-glucose derivative is taken up by using the images before and after the application of fLG.

A cell suspension taken is centrifuged onto a surface of the aforementioned glass or plastic plate to allow for adhesion of the cells. This centrifuge process can be achieved relatively easily when a commercially available automated cell collecting system with a cell centrifugation capability is used. During centrifugation, care must be taken not to dry the cells, but centrifugation may be performed up to 10 minutes when a buffer-solution holding structure (such as a silicone mask) configured not to lose liquid during centrifugation is used After the centrifugation, a small amount a KRB solution is added to the cell-attaching region to prevent dehydration of cells.

Below, the glass or plastic plate and the staining method after fluorescence observation will be described.

These may be applied both to a case where observation of a fluorescent substance is performed before adhesion of cells on the plate and a case where it is performed after adhesion. The cell of interest may be marked at its vicinity on the back side of the cell-attaching region on the glass or plastic plate used for the present invention to facilitate identification of the cell position.

At the back side of the cell-attaching region of the plate to be used, readable symbols, letters, lines, or the like may be pre-printed or pre-engraved on the glass of the back side. Use of this plate enables easy and accurate identification of cell positions. It is important that the cell-attaching region on the surface of a glass or plastic plate to be used has a structure capable of holding a certain amount of buffer solution so that cells can survive after centrifugation. The periphery of the cell-attaching region may be pre-enclosed with a water-repellent material such as silicone in order to effectively prevent dehydration of cells during operation and allow cells to be always immersed in a buffer solution. This enables operations without dehydrating cells regardless of experience and skills of cytotechnologists. Further, one of the four corners of the plate is preferably cut out at an angle to facilitate identification of the front or back and vertical or horizontal directions of the plate during operations.

A common inverted fluorescence microscope can be used for fluorescence and bright-field observation of the target cells present in the cell-attaching region on the plate. It is possible to conduct observation for at least about 1 hour at room temperature without having cell morphology changes which may interfere with the Papanicolaou staining. The glass plate is frequently moved in the vertical and horizontal directions to change views during microscopy, and thus a buffer solution added over the target cells may also move accordingly. This is particularly significant when an electric stage is used. Further, cells should be minimally affected by evaporation of the buffer solution. A mask (buffer-solution holding structure) having an opening comparable to or larger than the water-repellent enclosure around the cell-attaching region is tightly fitted on the glass surface, and an appropriate amount of the buffer solution depending on the desired observation duration is added to the opening. This can prevent dehydration and changes in osmotic pressure, even during prolonged microscopic observation.

After fluorescence observation, cells are fixed by adding a fixative such as ethanol to the cell-attaching region. The mask may be removed some time later after addition of the fixative to avoid detachment of cells due to the fixative. Then the glass plate may be allowed to stand in a fixative bath to further continue fixation. After fixation, the present glass plate may be subjected to common cell staining such as Papanicolaou staining and Giemsa staining according to the conventional procedures. Then a glass slide may be attached to the glass plate to prepare a permanent preparation, and then pathological cytodiagnosis may be performed in the same manner as the conventional way.

Comparison of the results from the common cell staining such as Papanicolaou staining and Giemsa staining as described above with the results from the fluorescence observation of the fluorescently labeled L-glucose derivative can be performed on the same cells by finding the positions of the target cells on the plate using the symbols, letters, lines, or the like provided on the back side of the plate as described above. The comparison can be performed more reliably by taking micrographs. Further, an electric XY stage may be used to record the positions over the target cells. In that case, an appropriate holder is required for maintaining the orientation and position of the glass plate on the stage constantly in the same manner. This holder needs to have a structure in which a thin glass plate can be conveniently and accurately fixed without damaging the plate. Further, depending on the magnification of the microscope, the errors may need to be corrected within the tolerance range of the shape of the glass plate. Either way, both in cases where manual stages are used and cases where electric stages are used, the symbols, letters, lines, or the like provided on the back side of the glass plate as described above enables views near the target cells to be identified repeatedly, quickly and reliably, and the target cells to be detected accurately and easily from the relative positional relationship regarding these symbols, letters, or lines.

In the method of detecting cancer cells according to the present invention, cancer cells are detected by observing fluorescence under a microscope. This enables identification of cancer cells otherwise missed by the conventional microscopy. Therefore, the occurrence of false negative due to human error can be reduced, and diagnosis accuracy can be improved. Further, cancer cells can be detected based on fluorescence, and thus fluorescence-emitting cells are preferentially observed with reduced risk of overlooking cells which require attention. This can increase the efficiency of the laboratory work and decrease the burden on cytotechnologists. Furthermore, the method based on detection of fluorescence according to the present invention enables automated detection.

Further, the method of detecting cancer cells according to the present invention can provide determination based on information about the presence or absence of functional anomalies of live cells, which is qualitatively different from information about morphological anomalies of cells on which the conventional cell determination solely relies.

According to another aspect of the present invention, the method of detecting cancer cells according to the present invention relates to a method for dual detection of cancer cells in which detection of cancer cells using the aforementioned fluorescently labeled L-glucose derivative is combined with detection of cancer cells based on conventional cytological staining such as Papanicolaou staining, Giemsa staining, or immunocytochemical staining (hereinafter, may simply be referred to as the "cytological staining of cancer cells").

In the method of detecting cancer cells using the aforementioned specific fluorescently labeled L-glucose derivative, cancer cells can be detected on a glass or plastic plate while maintaining the cells in a viable state, and the cytological staining of cancer cells described above can be then performed, enabling cancer diagnosis based on the dual detection method.

In that case, if markings for indicating cell positions are provided on the plate, it can be easily determined whether or not cancer cells detected by the fluorescently labeled L-glucose derivative according to the present invention is the same as cancer cells detected by the subsequent cytological staining of cancer cells. The combination of the detection of cancer cells based on cell functional anomalies and the detection of cancer cells based on cell morphological anomalies or marker detection can easily be performed on the same cells.

As described above, in the method for dual detection of cancer cells according to the present invention, cells which have undergone fluorescence observation is fixed, and then stained by a common staining method such as Papanicolaou staining or an immunocytochemical approach, enabling comparison with the results from these conventional technologies for the same cells as the fluorescently observed cells. Supplementing cell morphological information by the conventional technology with cell functional information from fluorescence observation can increase both the quality and quantity of information about cell conditions, improving diagnosis accuracy. This also can limit the number of cells to be observed, reducing the possibility of overlooking cells. Thereby, more accurate cancer diagnosis can be achieved.

Methods of staining cancer cells for cytological diagnosis which can be used in the present invention can include known methods in which cells are fixed on a glass plate, and then stained to detect cancer. They can include, but not limited to, for example, Papanicolaou staining, Giemsa staining, PAS staining, Grocott staining, and immunocytochemical staining with antibody against a cancer-specific marker. Papanicolaou staining is preferably used. These staining methods can be performed in accordance with the known procedures. As for immunocytochemical staining with antibody for distinguishing benign from malignant, the followings can be used: for example, p53, WT-1 (Wilm's tumor-1), IMP3, Ki-67, EMA (epithelial membrane antigen), CEA, cytokeratin, desmin, calretinin, D2-40 (podoplanin), TTF-1 (thyroid transcription factor), CD45, CD146, and the like.

One aspect of the present invention can provide a method of live-cell imaging in which living body-derived cells are attached on and held by a thin glass or plastic plate having a region capable of holding a buffer solution, and intracellular uptake of fluorescently labeled molecules is allowed while maintaining the cells in a viable state, and fluorescence from the fluorescently labeled molecules intracellularly present is detected.

One aspect of the method of live-cell imaging according to the present invention can provide a method including the following steps:
(Step A) a step of incubating living cells contained in a sample taken from a human with a fluorescently labeled compound,
(Step B) a step of stopping intracellular uptake of the fluorescently labeled compound,
(Step C) a step of allowing the cells to attach on a thin glass or plastic plate, the plate having a region for holding a buffer solution to maintain the cells in a viable state, and
(Step D) a step of detecting fluorescence from the fluorescently labeled compound present in the cells while maintaining the cells attaching to the plate in a viable state. The region on the surface of the glass or plastic plate for holding a buffer solution to maintain cells in a viable state in Step C may be provided either before or after cell adhesion. A plate in which such a region is provided before cell adhesion is preferably used.

There is no particular limitation for the fluorescently labeled molecules which can be used in Step A as long as they are fluorescently labeled molecules which can be specifically taken up into living cells.

It may be appropriately selected depending on the purposes of live-cell imaging. Examples can include, but not limited to, for example, 2-amino-2-deoxy L-glucose (2-NBDG) labeled with a fluorophore 7-nitrobenz-2-oxa-1,3-diazole group (NBD), which can be taken up into mammalian cells through glucose transporters with kinetics comparable to a radiolabeled D-glucose derivative (Nonpatent Document 1: Yamada et al., J. Biol. Chem. 275: 22278-83, 2000).

Incubation in Step A may be performed at a temperature of 22 to 37.5° C., preferably 36 to 37.5° C., more preferably about 37° C. The incubation duration can be appropriately selected depending on the purposes and the fluorescently labeled molecules to be used, but in general, it may be 15 minutes or less, preferably 3 to 15 minutes, more preferably 3 to 5 minutes.

Stopping uptake of the fluorescently labeled molecules in Step B may be performed according to the approach used in the method of detecting cancer cells according to the present invention.

Further, with regards to the glass or plastic plate, adhesion of cells on the plate, the buffer-solution holding structure, the buffer solution, the method of detecting fluorescence, and the like according to the present invention, such descriptions provided above in the context of the method of detecting cancer cells according to the present invention can also be applied to the method of live-cell imaging according to the present invention.

Another aspect of the present invention can provide a thin glass or plastic plate which can be used in the method of detecting cancer cells and/or the method of live-cell imaging of cells according to the present invention.

Still another aspect of the present invention can provide a buffer-solution holding structure, which can be applied to the above glass or plastic plate for sufficiently holding a buffer solution on the plate.

Yet another aspect of the present invention can provide a plate set for cell observation in which the above glass or plastic plate is combined with the above buffer-solution holding structure.

EXAMPLES

Below, the present invention will be described in detail with reference to Examples, but the present invention shall not be construed as limited to the followings.

It is noted that the studies were approved by the Ethics Committee of the Graduate School of Medicine, Hirosaki University, and were performed on subjects whose informed consents were obtained.

Example 1

Imaging of Cells in Peritoneal Washing From a Patient With Ovarian Cancer Using Fluorescently Labeled L-Glucose Derivative (Experimental Method)
(1) Preparation of Ascitic Fluid Immediately after the start of laparotomy for ovarian cancer (serous adenocarcinoma), the peritoneal cavity was washed with physiological saline for the purpose of collecting an ascitic fluid. A surplus portion of the resulting peritoneal washing was transferred into a 50 mL centrifuge tube. Subsequently, it was centrifuged at 1500 G for 2 minutes at room temperature, the supernatant was removed by decantation, and the pellet was dispersed by adding 2 mL of Krebs Ringer Buffer (KRB solution, see below) to obtain an ascites-cell suspension.

(1-1) KRB Solution

NaCl 129.0 mM, KCl 4.75 mM, $KH_2PO_4$ 1.19 mM, $MgSO_4.7H_2O$ 1.19 mM, $CaCl_2.2H_2O$ 1.0 mM, $NaHCO_3$ 5.02 mM, D-Glucose 5.6 mM, HEPES 10.0 mM (an adequate amount of 1M NaOH was added to adjust the pH to 7.35). In order to inhibit transport of fluorescently-labeled glucose through the gap junction/hemichannel, added was 0.1 mM carbenoxolone (Sigma, # C4790). It is noted that the KRB solution was used as a solution for preparing a solution of a fluorescently labeled L-glucose derivative (hereinafter, may be abbreviated as "fLG").

(2) Application of Fluorescently Labeled L-Glucose Derivative to Ascites Cells Obtained During Operation of Ovarian Cancer The above ascites-cell suspension in an amount of 1 mL was transferred into a 50 mL centrifuge tube, and 1 mL of the ×2 fLG solution described below was added and mixed, and the cells was exposed to fLG in a 37° C. water bath for 5 minutes. Then, 38 mL of a cold KRB solution at 0° C. was added to stop intracellular uptake of fLG, and centrifuged at 1500 G for 2 minutes at 0° C., and the supernatant was removed by decantation to lower the concentration of fLG. Again, 40 mL of the above cold KRB solution was added to the pellet to disperse the cells, and centrifuged at 1500 G for 1 minute at 0° C., and then the supernatant was removed. The cells were then dispersed in 5 mL of a cold KRB solution.

(2-1) Preparation of ×2 fLG Solution

A mixed solution of 2-NBDLG and 2-TRLG (fLG solution) was prepared in a KRB solution by dissolving them in accordance to the method described in Patent Document WO2012/133688 so that the concentrations of 2-NBDLG and 2-TRLG were 200 μM and 40 μM, respectively.

(3) Adhesion of Ascites Cells on Glass Plate by Centrifugation, and Maintenance of Cell Viability A glass plate cut into the size of a glass slide (FIG. 1C) was pre-mounted on a 6 ml chamber set (Sakura Finetek Japan Co., Ltd., composed of a plastic chamber, a metal chamber holder, a dedicated paper filter) dedicated for a commercially available automated cell collecting system CF-12D (Sakura Finetek Japan Co., Ltd.). Then, 5 mL of the ascites-cell suspension after application of fLG prepared in (2) was transferred to the plastic chamber dedicated for the above CF-12D, and centrifuged at 1400 rpm for 1 minute at room temperature.

After the centrifugation, the glass plate was quickly removed, and 0.2 mL of a KRB solution was immediately added to the cell-attaching region to prevent dehydration. Subsequently, a silicone-resin mask (see FIG. 1D) having an opening in a portion corresponding to the cell-attaching region was allowed to be tightly fitted on the glass plate, and 1 ml of a KRB solution was further added to the cell-attaching region to secure an amount of the buffer solution sufficient for maintaining the cells during live-cell imaging.

(3-1) Special Cover Glass for Live-Cell Imaging (Hereinafter Referred to as the "Glass Plate")

For the glass pate, used was No. 1S from Matsunaml Glass Ind., Ltd. (0.16 to 0.19 mm thick) cut into a size of 26 mm×76 mm as shown in FIGS. 1A and 1C. Further, the upper left corner of the glass plate was cut out at an angle for easy identification of back or front, up or down, and left or right. This cutout at an angle in the glass plate was sized such that when the present thin and fragile glass plate, instead of a slide glass, is mounted onto a Keyence slide-glass holder which is to be mounted on a microscope stage, the present glass plate would not be damaged by a hook of the holder side, and the errors in positions associated with placement of the glass plate in the holder would not interfere with identification of cells. Further, it was configured as follows: a rectangular water-repellent region was provided with a commercially available PAP pens for immunohistochemistry (such as a PAP pen liquid blocker, Ohmichi Co., Ltd.) so as to enclose the periphery of the cell-attaching region on the present glass plate in which a small amount (0.2 mL) of a KRB solution was able to be added and pooled to prevent dehydration of cells after the centrifugation of suspended ascites cells with an automated cell collecting system (FIG. 1C). The region drawn with a PAP pen as described above can be washed away with xylene contained in the embedding medium used during embedding after the fluorescence observation, and thus will not interfere with the Papanicolaou observation.

(3-2) Silicone Mask for Holding Buffer Solution (Buffer-Solution Holding Structure)

The mask (buffer-solution holding structure) tightly fitted on the glass plate for holding a buffer solution is made of silicone, has a thickness of 2 mm, is asymmetric in terms of up-down and left-right for easy identification of the orientation, is sized so as not to hide sample names and the like indicated on the glass plate, is configured to be easily fit tightly on the glass plate without generating air bubbles, and also easily removed without affecting the cell (FIGS. 1A and 1D). The mask can be fit and removed by holding an approximately 4 mm-large projecting portion provided on the upper part. The opening of the silicone mask is sized slightly larger than the enclosure provided around the cell-attaching region with a PAP pen. About 1 ml, of the KRB solution is to be instilled to it. Since the mask is thick and hydrophobic, the KRB solution will not spill flyer even when the electric stage and the like move quickly in the XYZ directions during microscopy. Further, it is configured such that the KRB solution can be added at any needed time when microscopy is performed for a prolonged time. This enables observation of cells while keeping them in good conditions. A stepped portion is provided at the right end of the mask. The above stepped portion is configured such that, when the glass plate on which the silicone mask instead of a slide-glass is tightly fitted is mounted on the Keyence glass slide holder, the thick silicone mask does not interfere with the projecting portion of the slide-glass holder.

(4) Image Acquisition

For fluorescence observation, observation and image acquisition were performed as follows after mounting the glass pate on a glass-slide holder dedicated for an all-in-one fluorescence microscope BZ-X700 (Keyence Corporation). First, the entire region of the cell-attaching region on the glass plate was observed by bright field microscopy using an ×20 lens (see below). A very small number of suspected cancer cells were found in this sample, and they were photographed. Bright field images and fluorescence images of the target cells were taken at a high magnification of 40× or 100×. Commercially available filters for BZ-X700 were used for fluorescence detection. A GFP filter for BZ-X (green channel, OP-87763, Ex 470/40 nm, Em 525/50 nm, DM 495 nm) was used for fluorescence observation of 2-NBDLG. A BZ-X TRITC filter (red channel, OP-87764, Ex 545/25 nm, Em 605/70 cm, DM 545 nm) was used for fluorescence observation of 2-TRLG. This suggests that the GFP filter used for fluorescence observation of 2-NBDLG in this Example transmits almost no fluorescence from 2-TRLG, allowing evaluation of uptake of 2-NBDLG while the TRITC filter used for fluorescence observation of 2-TRLG does transmit excitation light which can excite not only 2-TRLG but also 2-NBDLG slightly. Therefore, when fluorescence from 2-NBDLG is strong, fluorescence from 2-NBDLG may be mildly recognized in addition to fluorescence from 2-TRLG in the red channel, requiring cautions when results are interpreted. This problem can be significantly reduced when a fluorescence filter with an excitation light around 565 nm customized for 2-TRLG is used. It is noted that imaging conditions used in Examples are as follows.

×20 lens (CFI Plan Apo λ20×, #972032, NA 0.75, WD 1.00 mm)
Bright field image: monochrome, high sensitivity, transmitted illumination intensity 25, aperture stop 20%, exposure time 1/2500 sec
×40 lens (CFI Plan Apo λ40×, #972033, NA 0.95, WD 0.25 to 0.16 mm)
Bright field image: high sensitivity, transmitted illumination intensity 25, aperture stop 20%, exposure time 1/300 s
Green fluorescence image: high sensitivity, excitation light intensity 100%, exposure time 1/1.5 s
Red fluorescence image: high sensitivity, excitation light intensity 10%, exposure time 1/4 s
×100 lens (CFI Plan Apo λ100×, #972037, NA 1.45, ND 0.13 mm, oil immersion) in use
Bright field image: high sensitivity, transmitted illumination intensity 25, aperture stop 20%, exposure time 1/50 s
Green fluorescence image: high sensitivity, excitation light intensity 100%, exposure time 1/10 s
Red fluorescence image: high sensitivity, excitation light intensity 10%, exposure time 1/10 s (Experiment Results)

Imaging pictures obtained are shown in FIG. 2. FIG. 2A shows a bright-field image (the magnification at the objective lens is 100×) in which ascites cells obtained during an operation of a patient with ovarian cancer (serous adenocarcinoma) were subjected to microscopy while maintaining them in a viable state. Morphological observation identifies suspected cancer cells (those surrounded by a solid line at the center in the view) and apparently normal peritoneal mesothelial cells (those surrounded by a dotted line at the upper right in the view). FIG. 2B shows a fluorescence microscope image in the green wavelength region after application of the KRB solution containing 100 μM 2-NBDLG and 20 μM 2-TRLG. Morphologically suspected cancer cells at the center in the view (solid line) show intense fluorescence from 2-NBDLG while apparent peritoneal mesothelial cells (dotted line) at the upper right in the view do not show fluorescence from 2-NBDLG. FIG. 2C shows a similar image as in B described above. However, it shows a fluorescence microscope image in the red wavelength region. Cell debris at the left in the view shows intense red fluorescence from 2-TRLG. In contrast, neither the morphologically suspected cancer cells (solid line) at the center in the view nor the apparent peritoneal mesothelial cells (dotted line) at the upper right in the view show such red fluorescence. Therefore, it is highly unlikely that fluorescence from 2-NBDLG observed for the suspected cancer cells in B resulted from uptake due to damaged plasma membranes. It is noted that weak red fluorescence from the suspected cancer cells at the center in the view appears to reflect a component of a tail in the longer wavelength side of the intense 2-NBDLG fluorescence (see Nonpatent Document 1) passing through the fluorescence filter of the commercially available all-in-one type fluorescence microscope that was used FIG. 2D shows a superimposed image of the bright-field image and the fluorescence images. It clearly shows that green-fluorescent 2-NBDLG is selectively taken up into the suspected cancer cells, but not by the normal peritoneal mesothelial cells, and that cell debris at the left side are stained with red-fluorescent 2-TRLG.

Example 2

Correspondence of Live-Cell Fluorescence Imaging of Ascites Cells From a Patient with Endometrial Cancer After Application of the Fluorescently Labeled L-Glucose Derivative with Results From Papanicolaou Staining Performed After Fixation The fluorescently labeled L-glucose derivative was applied to ascites cells obtained during an operation of a patient with endometrial cancer, and live-cell fluorescence imaging was performed. Subsequently, the same sample was subjected to Papanicolaou staining after fixation of the cells. Then, correspondence between the both results was analyzed.
(Experimental Method)
(1) Preparation of Ascitic Fluid.
Immediately after the start of laparotomy for endometrial cancer (endometrioid adenocarcinoma), the peritoneal cavity was washed with physiological saline in the same manner as in Example 1 to obtain a peritoneal washing, which was then added to a 50 mL centrifuge tube having 5 mL of the Hanks solution in advance. The resulting ascitic fluid suspension was centrifuged at 1500 G for 2 minutes at room temperature, and the supernatant was removed by decantation. Subsequently, 30 mL of a commercially available solution of ammonium chloride for hemolysis was added, and allowed to stand for 2 minutes, and then centrifuged at 1500 G for 2 minutes at room temperature, and the supernatant was then removed by decantation. Some of the resulting pellet was set aside for cytodiagnosis tests at the hospital's pathology department, and the rest was further divided into 2 portions, each of which was dispersed into 40 mL of a KRB solution in 50 mL centrifuge tubes, and stored at room temperature an a dark place until application of fLG on the next day.

On the next day (about 20 hours after the ascites cells were obtained), the 50 ml centrifuge tubes containing 40 mL of the cell suspension, respectively, were centrifuged at 600 G for 1 minute at room temperature, and the supernatant was discarded by decantation, and 1 mL of a KRB solution was added to re-disperse the pellet.
(2) Application of Fluorescently Labeled L-Glucose Derivative to Ascites Cells of Endometrial Cancer.

An ×2 fLG solution prepared as in Example 1 (2-1) was added in an amount of 1 ml, and mixed, and the cells were exposed to fLG for 5 minutes in a 37° C. water bath. Then, 38 mL of a cold KRB solution at 0° C. was added to stop intracellular uptake of fLG, and centrifuged at 600 G for 1 minute at 0° C., and the supernatant was removed by decantation to decrease the concentration of fLG in the solution. Further, the cells were re-dispersed into 40 mL of a cold KRB solution, and again centrifuged at 600 G for 1 minute, and the supernatant was then removed. The ascites cells were then dispersed into 10 mL of a cold KRB solution.
(3) Adhesion of Ascites Cells on Glass Plate by Centrifugation, and Method of Maintaining Cell Viability It was performed as in Example 1 except that a glass plate having 3 marks pre-formed with a water-resistant pen on the back side of the cell-attaching region was used in order to further facilitate identification of cell positions on the glass plate. It is noted that marks for identification of cell positions may be pre-formed with intervals of 2 mm on the back side of the cell-attaching region on the glass plate in order to obtain cell positions more conveniently. This allows identification of cell positions to be much easier.
(4) Image Acquisition Conditions Observation and image acquisition were performed about 22 hours after obtaining ascites cells using the same instruments as in Example 1. The entire region of the cell-attaching region on the glass plate was subjected to bright-field microscopy with an ×10 lens (described below). The target cells and the markers provided on the back side of the glass plate were imaged in the same view to use the markers for identifying the position of the cells after Papanicolaou staining. Subsequently, a bright-field image and fluorescence images of the target cells were obtained using a high-power lens, and positional information on the stage was registered using a software dedicated for BZ-X700. Imaging conditions used are as follows.
×10 lens (CFI Plan Apo λ10×, #972031, NA 0.45, ND 4.00 mm) Bright field image: monochrome, high sensitivity, transmitted illumination intensity 25, aperture stop 20%, exposure time 1/4500 sec
For use of ×40 lens:
Bright field image: high sensitivity, transmitted illumination intensity 25, aperture stop 20%, exposure time 1/300 s
Green fluorescence image: high sensitivity, excitation light intensity 100%, exposure time 1/4 s
Red fluorescence image: high sensitivity, excitation light intensity 10%, exposure time 1/10 s
For use of ×100 lens:
Bright field image: high sensitivity, transmitted illumination intensity 25, aperture stop 20%, exposure time 1/50 s
Green fluorescence image: high sensitivity, excitation light intensity 100%, exposure time 1/4 s
Red fluorescence image: high sensitivity, excitation light intensity 10%, exposure time 1/10 s
(5) Papanicolaou Staining and Observation After fluorescence observation, the glass plate was immersed into a container filled with 99.5% ethanol and allowed to stand for 5 minutes, and then the silicone mask was removed. After ethanol fixation, Papanicolaou staining was performed according to the conventional procedures, and a glass slide was fit and sealed on the glass plate upside down, as contrary to the usual, to prepare a permanent preparation. In order to perform bright-field observation of the target cells imaged during fluorescence observation in the same view based on the registered positional information on the stage, the edge of the glass plate was precisely aligned with that of the glass slide when they were fit together. For post-staining observation, the view was roughly examined with a help of the markers under a normal upright microscope, and then identification of the view was again performed based on the positional information registered in the BZ-X700 all-in-one fluorescence microscope, and observation and image acquisition were performed with an ×40 lens. Imaging conditions used are as follows: bright-field color, high resolution, transmitted illumination intensity 25, aperture stop 20%, and exposure time 1/1.5 s.

(Experiment Results)

Results from correspondence of the result form live-cell imaging of the ascites cells obtained during an operation of a patient with endometrial cancer (endometrioid adenocarcinoma) with the results from the subsequent Papanicolaou staining are shown in FIGS. 3 and 4. FIG. 3A shows a bright-field image (the magnification at the objective is 40×) of two living-cell clusters which were suspected to be cancer cells based on morphological observation. fLG was applied on the next day after obtainment of the ascitic fluid (after about 20 hours), and image acquisition was performed after about 22 hours. The black portion at the upper right in the view represents a part of the marks for positional identification provided on the back side of the glass plate. FIG. 3B shows a fluorescence microscope image in the green wavelength region after application of the KRB solution containing 100 µM 2-NBDLG and 20 µM 2-TRLG. It clearly indicates that both of the two cancer-cell clusters, one at the left and the other at the right in the view, show fluorescence from 2-NBDLG. FIG. 3C is similar to FIG. 3B except that it shows a fluorescence microscope image in the red wavelength region. The cell cluster at the left side in the view shows red fluorescence from 2-TRLG, suggesting that some of the 2-NBDLG fluorescence observed from the cells determined as suspected cancer cells in B may be fluorescence resulting from uptake due to damaged plasma membranes, while the cell cluster (Cluster 1) at the right side in the view does not show red fluorescence from the 2-TRLG, excluding the possibility that the 2-NBDLG fluorescence resulted from uptake due to damaged plasma membranes. FIG. 3D shows an enlarged view of the bright-field image (the magnification at objective lens is 100×) of the cell cluster at the right side in the view (Cluster1) in C. FIG. 4A shows an enlarged fluorescence microscope image in the green wavelength region of the cell cluster at the right side of the view in FIG. 3B (Cluster 1). It shows that 2-NBDLG is taken up into the cytoplasmic portion except for the nucleus. FIG. 4B shows an enlarged fluorescence microscope image in the red wavelength region of the cell cluster (Cluster 1) at the right side of the view in FIG. 3C. Red fluorescence from 2-TRLG is not observed. FIG. 4C shows a superimposed image of the bright-field image and fluorescence images of the cell cluster (Cluster 1) in FIG. 3D, FIG. 4A, and FIG. 4B. FIG. 4D shows a bright-field image of the cell cluster (Cluster 1) shown in FIG. 3D, FIG. 4A, and FIG. 4B, i.e., a cell cluster positive for 2-NBDLG but negative for 2-TRLG after subjected to Papanicolaou staining. This indicates that the cell cluster has nucleus morphology and cell clustering morphology characteristic of typical adenocarcinoma cells based on the cytological classification.

Example 3

Correspondence of Live-Cell Fluorescence Imaging of Ascites Cells from a Patient With Endometrial Cancer After Application of the Fluorescently Labeled L-Glucose Derivative with Results from Papanicolaou Staining Performed After Fixation The fluorescently labeled L-glucose derivative was applied to ascites cells obtained during an operation of a patient with endometrial cancer, and live-cell fluorescence imaging was performed. Subsequently, the same sample was subjected to Papanicolaou staining after fixation of the cells. Then, correspondence between the both results was analyzed. This is an example where cells determined to be reactive mesothelial cells were observed.

(Experimental Method)

(1) Preparation of Ascitic Fluid

Immediately after the start of laparotomy for endometrial cancer, the peritoneal cavity was washed with physiological saline in the same manner as in Example 1 to obtain a peritoneal washing, which was then added to a 50 mL centrifuge tube having 5 mL of the Hanks solution in advance. The resulting ascitic fluid suspension was centrifuged at 1500 G for 2 minutes at room temperature, and then the supernatant was removed with a dropper. Some of the resulting pellet was set aside for cytodiagnosis tests at the hospital's pathology department, and the rest was dispersed into 15 mL of a KRB solution in a 15 mL centrifuge tube, then again centrifuged at 1500 G for 2 minutes at room temperature, and the supernatant was removed with a dropper. The pellet primarily includes red blood cells, and a large amount of red blood cells may obscure the target cells, interfering with microscopy. Red blood cells, which have a high specific gravity, are spinned down at the bottom of a centrifuge tube, and a layer (buffy coat) including components such as target cells, white blood cells, and platelets is formed thereover. Therefore, one third of a portion above the pellet including the buffy coat was collected with a dropper in order to reduce the amount of red blood cells, dispersed into 15 mL of a KRB solution in a 50 mL centrifuge tube, and was stored in a dark place at room temperature until application of fLG.

A 50 mL centrifuge tube containing 15 mL of the cell suspension was centrifuged at 600 G for 1 minute at room temperature, the supernatant was then discarded by decantation, and 1 mL of a KRB solution was added to the pellet and re-dispersed.

(2) Application of Fluorescently Labeled L-Glucose Derivative to Ascites Cells of Endometrial Cancer An ×2 fLG solution prepared as in Example 1 (2-1) in an amount of 1 mL was added and mixed, and the cells was exposed to fLG for 5 minutes in a 37° C. water bath. Then, 38 mL of a cold KRB solution at 0° C. was added to stop intracellular uptake of fLG, and centrifuged at 650 G for 1 minute at 0° C., and the supernatant was removed by decantation to decrease the concentration of fLG in the solution. Further, the cells were re-dispersed into 40 mL of a cold KRB solution, and again centrifuged at 650 G for 1 minute, and the supernatant was then removed. Then, the ascites cells were dispersed into 10 mL of a cold KRB solution. It is noted that adhesion of the ascites cells on the glass plate by centrifugation and the method of maintaining viability as well as Papanicolaou staining and observation were performed in a similar way as in Example 2. Images were obtained with an ×40 lens, and image acquisition conditions were as follows. Bright field image: high sensitivity, transmitted illumination intensity 25, aperture stop 20%, exposure time 1/500 s
Green fluorescence image: high sensitivity, excitation light intensity 100%, exposure time 1/4 s
Red fluorescence image: high sensitivity, excitation light intensity 10%, exposure time 1/10 s
(Experiment Results)

FIG. 5 shows an enlarged view of a region containing reactive mesothelial cells observed after live-cell fluorescence imaging and Papanicolaou staining. FIG. 5A shows a fluorescence microscope image (the magnification at the objective lens is 40×) in the green wavelength region after application of the KRB solution containing 100 μM 2-NBDLG and 20 μM 2-TRLG. A cell population present in the region of interest surrounded by a white line shows fluorescence from 2-NBDLG. Intense fluorescence at the right to the region of interest represents an insoluble substance showing green fluorescence. FIG. 5B is similar to A except that it shows a fluorescence microscope image in the red wavelength region. The cell population in the region of interest does not show red fluorescence from 2-TRLG, suggesting that the high unlikeliness of the 2-NBDLG fluorescence resulting from uptake due to damaged plasma membrane. FIG. 5C shows a bright-field image over which the fluorescence images of A and B are superimposed. FIG. 5D shows results from Papanicolaou staining performed after fluorescence staining. The cell population in the region of interest surrounded by a white line in A to C appears to show nucleus morphology and cell clustering morphology characteristic of apparent reactive mesothelial cells. If a cell population with a large N/C ratio is observed in an cytodiagnosis sample from an ascitic fluid as described in this example, diagnosis based on the presence of anisokaryosis and polarity, morphologies of nucleolus and chromatin, the size of a cell itself, or cell clustering morphology may be significantly subjective on whether the cell population includes reactive mesothelial cells or abnormal cells suspected to have possibility of progression to cancer, or whether it corresponds to an inconclusive case. In other words, the borderline between reactive mesothelial cells and abnormal cells suspected to have possibility of progression to cancer is likely to vary widely depending on the individual cytotechnologists and board certified cytopathologists. The present invention can provide qualitatively different information than the conventional cytological determination solely based on information about morphological anomalies of cells. The present invention can also provide information useful for benign-malignant determination of such cells by studying the course and prognosis of cancer.

Example 4

Correspondence of Live-Cell Fluorescence Imaging in which the Fluorescently Labeled L-Glucose Derivative was Applied to the Original Ascites Cells From a Parent with Ovarian Cancer by the Perfusion Method with the Results From Papanicolaou Staining Performed After Fixation The fluorescently labeled L-glucose derivative was applied to the ascites cells obtained during an operation of a patient with ovarian cancer, and live-cell fluorescence imaging was performed, and then the same sample was subjected to Papanicolaou staining after fixation of the cells. Then, correspondence between the two results was analyzed.

(Experimental Method)
(1) Preparation of Ascitic Fluid

A surplus portion of the original ascitic fluid taken from the peritoneal cavity immediately after the start of laparotomy for ovarian cancer (serous adenocarcinoma) was added to a 50 mL centrifuge tube having 5 mL of the Hanks solution in advance. The obtained ascitic fluid suspension was checked for presence of fibrin with a toothpick, and then passed through a mesh to remove fat and impurities. Next, it was evenly dispensed into two 50 mL centrifuge tubes, and centrifuged at 1500 G for 2 minutes at room temperature. The supernatant of each of the two centrifuge tubes was then gently removed from the liquid surface down to 7.5 mL with an electric pipette, and then the rest was further removed with a dropper to leave 1 mL. The sedimented layer containing red blood cells and the like were present at the bottom of the centrifuge tube. A 1 mL portion was collected from the upper surface with a dropper without aspirating red blood cells from the sedimented layer to obtain an ascites cell suspension.

(2) Adhesion of Ascites Cells on Glass Plate by Centrifugation, and Method of Maintaining Cell Viability The ascites cells were allowed to attach on a glass plate using a commercially available automated cell collecting system CF-12D (Sakura Finetek Japan Co., Ltd.). Specifically, a glass plate (FIG. 14) cut into a size of 25.7×75.0 mm tightly pre-fitted with a silicone mask for perfusion (FIG. 15, composed of an outer mask and an inner mask) was mounted on a 1 mL chamber set (Sakura Finetek Japan Co., Ltd., a plastic chamber) dedicated to the system. Then, 1 mL of the ascites cell suspension prepared in (1) was transferred to the plastic chamber dedicated for the aforementioned CF-12D, and was centrifuged at 1400 rpm for 1 minute at room temperature. After the centrifugation, the glass plate was quickly removed, and a KRB solution was immediately added to the cell-attaching region to prevent dehydration. Then, the inner mask having an opening at a position corresponding to the cell-attaching region was removed, and a KRB solution was further added to the fish-like opening of the outer mask to secure a sufficient amount of the buffer solution for maintaining the cells during live-cell imaging. For smooth perfusion, a cover glass (MATSUNAMI MICRO COVER GLASS: 22×22 mm) sized such that the fish-like opening is not completely covered was tightly fitted, and then stored in a moisture chamber until being mounted on the perfusion stage.

(2-1) Special Cover Glass (Glass Plate) for Live-Cell Imaging by Perfusion

As the glass plate, a No. 1S from Matsunami Glass Ind., Ltd. (0.16 to 0.19 mm thick) cut into a size of 25.7 mm×75.0 mm as shown in FIGS. 1A and 1C was used. Further, the upper left corner of the glass plate was cut out at an angle for easy identification of front or back, up or down, and left or right. This cutout at an angle of the glass plate was sized such that when the present thin and fragile glass plate is mounted on the custom perfusion stage from System Instruments Co., Ltd., which is to be mounted for use on the microscope stage, the errors in positions would not result in difficult identification of cells.

(2-2) Silicone Mask for Perfusion (Buffer-Solution Holding Structure)

Figure 15:
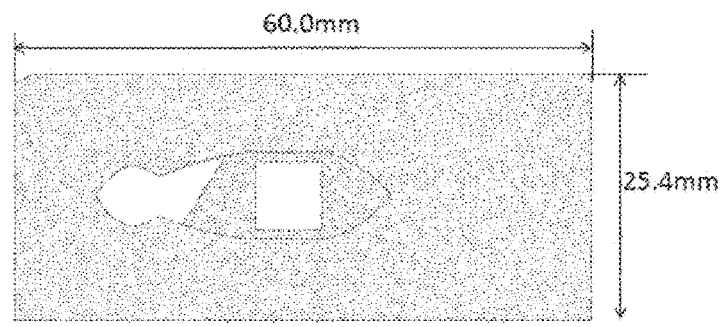
FIG. 15 shows a silicone mask for perfusion (buffer-solution holding structure). An inner mask located in the inner portion is configured to have an opening which coincides with the cell-attaching region. An outer mask is tightly fitted with the outer portion of the inner mask. During perfusion, the inner mask is removed while the outer mask alone remains. The opening of the outer mask has a fish-like shape to facilitate a smooth perfusion of a solution.

The mask tightly fitted on the glass plate intended for holding a buffer solution is made of silicone, and has a thickness of 0.5 mm, and is asymmetric in terms of up-down and left-right for easy identification of the orientation, and is sized so as not to hide sample names and the like indicated on the glass plate, and is configured so that it can be easily and tightly fitted on the glass plate without generating air bubbles and also easily removed without affecting the cells (FIGS. 14 and 15). The present silicone mask has a nested structure of an inner mask having an opening which has the same size as the cell-attaching region, and an outer mask having a fish-like opening into which the inner mask can be fit. The opening of the inner mask has the same size as a frame line surrounding the cell-attaching region so that the outflow of cells into a region other than the cell-attaching region can be prevented when cell adhesion by centrifugation is performed. A cover glass sized so as not to block the opening after cell adhesion is attached to the fish-like opening of the outer mask. This enables just sufficient perfusion in which, when the fish-head side is defined as Inlet, and the tail side is defined as Outlet, a solution flowing from the Inlet side spontaneously flows to the Outlet side without spillover in the Inlet side.

(3) Attachment of Glass Plate on Perfusion Stage and Perfusion

Figure 16:
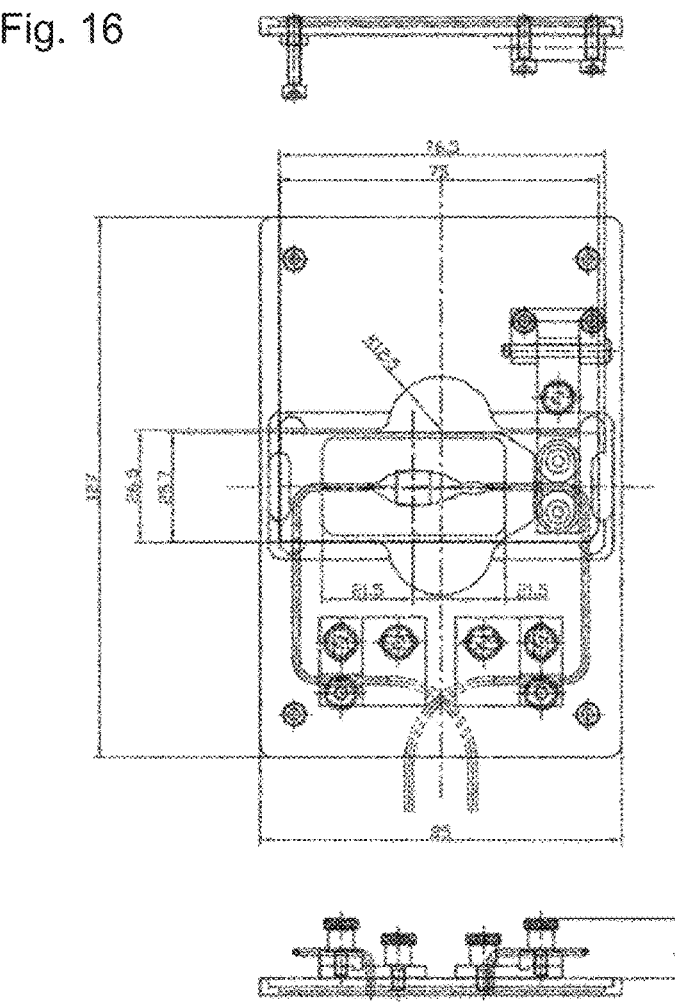
FIG. 16 shows a perfusion stage (System Instruments Co., Ltd.). Slide plates are arranged in the left and right portions so that the positions of metal tubes at the Inlet and Outlet sides of the KRB solution can be fixed and finely adjusted when a glass plate is placed at the central portion. The perfusion stage is mounted on a BZ-X700 microscope through a stage top incubator (INUG2-KIW, TOKAI HIT Co., Ltd.,) shown in FIG. 15.
Figure 17:
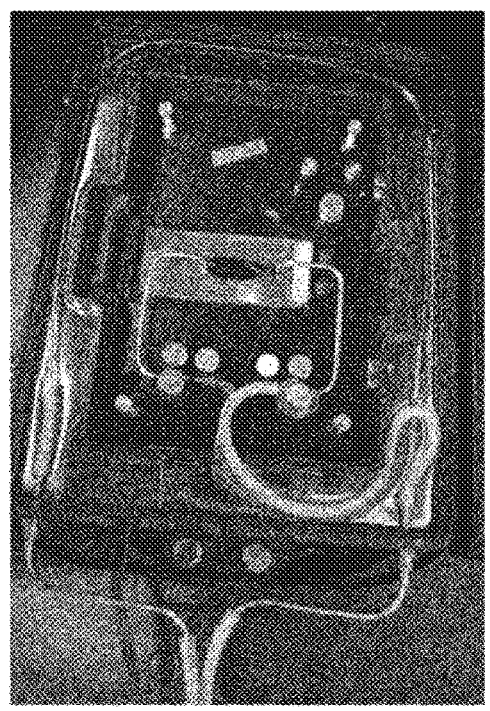
FIG. 17 shows an image during perfusion of a KRB solution in which the stage top incubator (INUG2-KIW, TOKAI HIT Co., Ltd.,) and then the perfusion stage of FIG. 14 are mounted on the BZ-X700 microscope, and then the glass plate is mounted.

A stage top incubator (INUG2-KIW, TOKAI HIT Co., Ltd.) was mounted on BZ-X700 before the completion of preparation of an ascites-cell suspension. Then, a perfusion stage (FIGS. 16, 17) was mounted, and subsequently a perfusion pump (ISMATEC) was connected to the perfusion line. A KRB solution was used for perfusion, and the source bottle of the solution was pre-warmed in a 40° C. water bath to prevent air bubbles dissolved in the solution from entering into the perfusion line. An air trap is also provided at the beginning of the line to further prevent inflow of air bubbles. A dummy glass plate was mounted on the perfusion stage to perform perfusion with the KRB solution, and settings were adjusted so that the temperature in the cell-attaching portion was 37.0±0.5° C. at a flow rate of 0.7 mL/min. Specifically, the temperatures of the top heater and the bath heater of the stage top incubator were selected so that the inside of the incubator was maintained at a constant temperature. Further, about 40 mL of water was poured into the water channel located inside the incubator and was heated at the same time. A thin stainless steel tube was arranged along the channel, and the KRB solution was allowed to flow through the tube to warm the KRB solution before reaching the cells. The glass plate on which cells had been attached was mounted on the perfusion stage so that the portion corresponding to the head of the fish-like opening of the silicone mask for perfusion was positioned at the Inlet side of the perfusion system, and a portion corresponding to the tail of the opening was positioned at the Outlet side. Perfusion was started at a flow rate of 0.3 mL/min, and perfusion conditions and cell-adhesion conditions were observed by bright-field microscopy at the time of the start of perfusion. Subsequently, the flow rate was increased by 0.1 mL/min every other minute up to 0.7 mL/min to ensure stable perfusion.

(4) Application of Fluorescently Labeled L-Glucose Derivative to Ascites Cells, and Acquisition of Images Images was acquired by a tiling approach in which images were taken within a specified range while slightly shifting the view in the horizontal direction instead of manually taking images at several positions. Specifically, the entire view of the cell-attaching region of the cover glass for cell observation was first acquired with an ×10 lens. Then, the lens was changed to an ×40 lens, and the imaging, range and the focus was determined by specifying three points. Specifically, the upper left of the frame line surrounding the cell-attaching region was defined as A, and the range was arranged so that the frame was positioned at the left end in the view. Further, a portion above the cell-attaching glass surface by 6.3 microns was selected as the imaging surface. The view was shifted to the right, and arrangements were made in the same manner so that the next frame corner corresponded to B, and the diagonal of A corresponded to C. The imaging region was determined by the 2 points of A and C, and a portion above the cell-attaching glass surface by 6.3 microns was determined as the imaging surface by the 3 points of A, B, and C. The reason for using a portion above the cell-attaching glass surface by 6.3 microns as an imaging surface is that cancer cells generally form one or more three-dimensional structures having a certain height, and thus focusing at the height of the glass surface may not be appropriate for observing their nuclei and cytoplasms. These operations will generate 1036 (28×37) images with a view of the ×40 dens during image acquisition, allowing imaging of the entire view of the cell-attaching region in about 3 minutes and 30 seconds. These images may be combined together with a specialized application software during image analysis (image joint) to obtain one large image. Green fluorescence images and then bright-field images of the fluorescently labeled L-glucose derivative before administration were taken under the following conditions.

Green fluorescence image: high sensitivity (Gain 6 db, Binning 3×3), excitation light intensity 100%, exposure time 1/80 s Bright field image: high sensitivity (Gain 6 db, Binning 3×3), transmitted illumination intensity 25%, aperture stop 20%, exposure time 1/500 s Administration of Fluorescently Labeled L-Glucose Derivative (4-1) Preparation of Solution of Fluorescently Labeled L-Glucose Derivative A mixed solution of 2-NBDLG and 2-TRLG (fLG solution) was prepared in a KRB solution by dissolving them in accordance to the method described in Patent Document WO2012/133688 so that the concentrations of 2-NBDLG and 2-TRLG were 100 µM and 20 µM, respectively. The fLG solution was supplied through a different line branched from the KRB solution. The fLG solution was pre-warmed to 40° C. in a water bath in a similar way as in the KRB solution to lightly remove air in the liquid, and then was passed through an air trap, and joined with the line of the KRB solution before a perfusion pump. Administration continued for 5 minutes, and then the imaging surface was re-adjusted in the same manner as in (4) just before image acquisition. Images were then taken 10 minutes after the solution was switched to the KRB solution in the order of green, red, and bright field under the following conditions.

Green fluorescence image: high sensitivity, excitation light intensity 100%, exposure time 1/80 s Red fluorescence image: high sensitivity, excitation light intensity 5%, exposure time 1/120 s Bright field image: high sensitivity, transmitted illumination intensity 25%, aperture stop 20%, exposure time 1/500 s (5) Papanicolaou Staining and Observation After fluorescence observation, the cover glass for cell observation was immersed into 99.5% ethanol in a container, and allowed to stand for 5 minutes, and then the silicone mask for perfusion was removed. After fixation with ethanol, Papanicolaou staining was performed in accordance with the conventional method. A cover glass for cell observation was then attached and sealed on the glass slide to obtain a permanent preparation. In order to combine images taken during fluorescence observation with an image taken after Papanicolaou staining, the edge of the cover glass for cell observation was precisely aligned with that of the glass slide when they were fit together. Post-staining observation was performed as follows: the sealed cover glass for cell observation was mounted on the perfusion stage, and the acquisition range and imaging surface were adjusted as in the image acquisition during perfusion. The imaging conditions were as follows: bright-field color, high resolution (Gain 6 db, Binning 1×1), transmitted illumination intensity 100%, aperture stop 20%, and exposure time 1/7.5 s.
(Experiment Results)

Results from correspondence of the results from live-cell imaging of the ascites cells obtained during an operation of a patient with ovarian cancer (serous adenocarcinoma) with the results from the subsequent Papanicolaou staining are shown in FIGS. 6, 7, 8, and 9. FIG. 6A shows a superimposed image of a fluorescence image in the green wavelength region, a fluorescence image in the red wavelength region, and a bright-field image of the entire cell-attaching region before application of fLG, and FIG. 6B shows a superimposed image of a fluorescence image in the green wavelength region, a fluorescence image in the red wavelength region, and a bright-field image after application of fLG. Morphological observation of the Papanicolaou staining image in FIG. 8D and an enlarged view thereof, which is FIG. 9, indicates that the cell cluster has characteristics of cancer cells. That is, characteristics such as large cell bodies, large nuclei, high N/C ratio to cytoplasm, and condensed chromatin are observed. FIG. 7A shows a fluorescence microscope image in the green wavelength region of the cell cluster shown in FIG. 8D before application of fLG, while FIG. 7B shows a fluorescence microscope image in the green wavelength region after application of fLG.

Comparison of the two images indicates that the cancer cell cluster shows fluorescence from 2-NBDLG. FIG. 8B shows a fluorescence microscope image in the red wavelength region of a similar cell cluster after application of fLG, but does not show red fluorescence from 2-TRLG. Therefore, it is highly unlikely that the 2-NBDLG fluorescence from this cell cluster resulted from uptake due to damaged plasma membranes. That is, the cell cluster determined to have nucleus morphology and cell clustering morphology indicative of cancer cells based on cytological diagnosis after Papanicolaou staining is positive for 2-NBDLG and negative for 2-TRLG, demonstrating that the method of physiologically detecting cancer cells according to the present invention is consistent with the morphological diagnosis method.

Example 5

Correspondence of Live-Cell Fluorescence Imaging of Cells in Peritoneal Washing From a Patient with Endometrial Cancer After Applying the Fluorescently Labeled L-Glucose Derivative by Perfusion with Results from Papanicolaou Staining Performed After Fixation The fluorescently labeled L-glucose derivative was applied to the cells in peritoneal washing obtained during an operation of a patient with endometrial cancer, and live-cell fluorescence imaging was performed. Subsequently, the same sample subjected to Papanicolaou staining after fixation of the cells. Then, correspondence between the both results was analyzed.
(Experimental Method)
(1) Preparation of Peritoneal Washing A peritoneal washing obtained immediately after the start of laparotomy for endometrial cancer (endometrial endometrioid adenocarcinoma) in the same manner as in Example 1 was added to a 50 mL centrifuge tube having 5 mL of the Hanks solution in advance. Fibrin, fat, and impurities were removed from the ascitic fluid suspension in the same manner as in Example 4. Subsequently, a half of it was dispensed into a 50 mL centrifuge tube, and centrifuged at 1500 G for 2 minutes at room temperature. The supernatant was processed in the same manner as in Example 4 to obtain 1 mL of an ascites-cell suspension.
(2) Adhesion of Ascites Cells on Glass Plate by Centrifugation, and Method of Maintaining Cell Viability The ascites-cell suspension in an amount of 1 mL taken at (1) was transferred to a plastic chamber dedicated for CF-12D as in Example 4. The ascites cells were allowed to attach on a glass plate by centrifugation at 1400 rpm for 1 minute at room temperature. The plate was then treated as in Example 4, and stored in a moisture chamber until being mounted on the perfusion stage.
(3) Attachment of Glass Plate on Perfusion Stage and Perfusion It was performed as in Example 4.
(4) Application of Fluorescently Labeled L-Glucose Derivative to Cells in Peritoneal Washing, and Acquisition of Images It was performed as in Example 4. Only a green fluorescence image was taken before administration of the fluorescently labeled L-glucose derivative. Further, the fLG solution was administered for 5 minutes. 10 minutes after the solution was switched to a KRB solution, post-administration images were taken in the order of green, red, and bright field. Papanicolaou staining after ethanol fixation was performed in the same manner.
(Experiment Results)

Results from correspondence of the results from live-cell imaging of the cells in peritoneal washing obtained during an operation of a patient with endometrial cancer (endometrial endometrioid adenocarcinoma) and the results from the subsequent Papanicolaou staining are shown in FIGS. 10, 11, 12, and 13. FIG. 10A shows a superimposed image of a fluorescence image in the green wavelength region, a fluorescence image in the red wavelength region, and a bright-field image of the entire cell-attaching region before application of fLG, and FIG. 10B shows a superimposed image of a fluorescence image in the green wavelength region, a fluorescence image in the red wavelength region, and a bright-field image after application of fLG. The morphological observation of FIGS. 11C, 11D, 12D, 13*a*, and 13*b* identifies apparent mesothelial cells and apparent macrophage cells (cell clusters at a and b). FIG. 11B shows a fluorescence microscope image in the green wavelength region after application of the KRB solution containing 100 μM 2-NBDLG and 20 μM 2-TRLG. Neither the cell cluster a nor b shows fluorescence from 2-NBDLG as compared with the image before application in FIG. 11A. Further, neither a nor b shows red fluorescence in the fluorescence image in the red wavelength region in FIG. 12B. These results indicate that 2-NBDLG is not taken up into normal mesothelial cells and macrophage cells having undamaged plasma membranes. FIG. 12D and enlarged views thereof, which are FIGS. 13*a* and 13*b*, show results from Papanicolaou staining performed after fluorescence staining. The results show characteristics such as large cell bodies, evenly sized nuclei, and a small N/C. Further, the staining results shows that the cells received less damage due to denatured nucleus and clustering, and that the staining does not interfere with morphological determination by cytotechnologists and board certified cytopathologists in any way, demonstrating that the perfusion method is effective.

The detailed descriptions shown above are merely intended for illustrating the object and target of the present invention, and shall not be construed as limiting the scope of the accompanying claim. In the view of the teachings described herein, it will be obvious to a person skilled in the art that various modifications and substitutions may be made to the embodiments disclosed herein without departing from the scope of the present invention.

INDUSTRIAL APPLICABILITY

The method according to the present invention can provide a novel cytodiagnosis method in which living-body derived cells can be imaged in viable conditions. Further, the present invention can provide a method for dual detection of cancer cells in which detection of cancer cells by live-cell imaging is combined with an existing method of cytologically diagnosing cancer cells, such as the Papanicolaou staining method or the Giemsa staining method.

The invention claimed is:

1. A method for imaging a living cell in a sample taken from a human, comprising:
   (a-1) incubating a cell mass comprising a living cell contained in the sample taken from the human in a buffer solution containing a fluorescently labeled molecule which can be taken up into a living cell to allow for uptake of the fluorescently labeled molecule,
   (a-2) replacing the buffer solution with a buffer solution free from the fluorescently labeled molecule to stop the uptake of the fluorescently labeled molecule,
   (a-3) allowing the cell mass to attach to a cell-attaching region on a thin glass or plastic plate, and adding the buffer solution to a buffer-solution holding region for holding the buffer solution configured to include and enclose the cell-attaching region and provided on the plate, and maintaining the cell in a viable state, wherein the buffer-solution holding region comprises a plate side for cell adhesion and a buffer-solution holding structure configured to enclose the buffer-solution holding region,
   (a-4) detecting fluorescence from the fluorescently labeled molecule present inside the attached living cell in the attached cell mass,
   wherein the cell mass is obtained from a cell suspension, obtained from exfoliative denuded cells, or obtained from fine-needle aspirated cells.

2. The method according to claim 1, wherein the cell mass is obtained from a cell suspension selected from expectoration, urine, ascitic fluid, pleural fluid, pericardial fluid, cerebrospinal fluid, bile, pancreatic fluid, synovial fluid, or blood of a patient.

3. The method according to claim 1, wherein the cell mass is obtained from an ascitic fluid of a patient having ovarian cancer or endometrial cancer.

4. The method according to claim 1, wherein the fluorescently labeled molecule is a fluorescently labeled L-glucose derivative having a 7-nitrobenz-2-oxa-1,3-diazole group or a derivative thereof as a fluorophore on the molecule thereof.

5. The method according to claim 1, wherein the buffer-solution holding structure is a plate-like or ring-like structure having an opening corresponding to the buffer-solution holding region, and has a thickness sufficient to hold the buffer solution.

6. A method for dual detection of a cancer cell in a sample taken from a human, comprising:
   (a) the method according to claim 1, and
   (b) a method of detecting cancer based on staining of a cell fixed with alcohol, comprising the step of:
   immersing a plate into an alcohol fixing liquid to fix the cell, and then performing staining by any one method selected from the group consisting of Papanicolaou staining, Giemsa staining, PAS staining, Grocott staining, and immunocytochemical staining to detect the cancer cell,
   wherein the cancer cell detected in method (a) and the cancer cell detected in method (b) are the same cancer cell.

7. The method of claim 1, wherein step (a-3) comprises performing centrifugation to attach the cell mass to the cell-attaching region.

8. A method for imaging a living cell in a sample taken from a human, comprising:
   (a-1) allowing a cell mass comprising a living cell contained in the sample taken from the human to attach to a cell-attaching region on a thin glass or plastic plate,
   (a-2) adding a buffer solution to a buffer-solution holding region for holding the buffer solution configured to include and enclose the cell-attaching region and provided on the plate, and maintaining the cell in a viable state, wherein the buffer-solution holding region comprises a plate side for cell adhesion and a buffer-solution holding structure configured to enclose the buffer-solution holding region,
   (a-3) replacing the buffer solution with a buffer solution containing a fluorescently labeled molecule which can be taken up into a living cell, and then bringing the cell mass attached to the plate into contact with the fluorescently labeled molecule to allow for uptake of the fluorescently labeled molecule,
   (a-4) replacing the buffer solution with a buffer solution free from the fluorescently labeled molecule to stop the uptake of the fluorescently labeled molecule, and detecting fluorescence from the fluorescently labeled molecule present inside the living cell in the attached cell mass,
   wherein the cell mass is obtained from a cell suspension, obtained from exfoliative denuded cells, or obtained from fine-needle aspirated cells.

9. The method according to claim 8, wherein the fluorescently labeled molecule is a fluorescently labeled L-glucose derivative having a 7-nitrobenz-2-oxa-1,3-diazole group or a derivative thereof as a fluorophore on the molecule thereof.

10. The method according to claim 8, wherein the fluorescently labeled L-glucose derivative is a mixture of 2-[N-(7-nitrobenz-2-oxa-1,3-diazole-4-yl)amino]-2-deoxy-L-glucose (2-NBDLG) and 2-amino-2-deoxy-L-glucose (2-TRLG) in which sulforhodamine 101 is bonded at position 2 via a sulfonamide bond.

11. The method according to claim 8, wherein detecting fluorescence in step (a-4) further comprises determining the degree of damage on a plasma membrane of the cell in the attached cell mass with reference to a fluorescence color tone of the cell in the attached cell mass.

12. The method according to claim 8, wherein the buffer-solution holding structure is a plate-like or ring-like structure having an opening corresponding to the buffer-solution holding region, and has a thickness sufficient to hold the buffer solution.

13. The method according to claim 12, wherein the buffer-solution holding structure is made of silicone, and has a thickness of 0.5 to 10 mm.

14. The method according to claim 8, wherein the plate has a thickness of 0.3 mm or less.

15. A method for dual detection of a cancer cell in a sample taken from a human, comprising:
   (a) the method according to claim 8, and
   (b) a method of detecting cancer based on staining of a cell fixed with alcohol, comprising the step of:

immersing a plate into an alcohol fixing liquid to fix the cell, and then performing staining by any one method selected from the group consisting of Papanicolaou staining, Giemsa staining, PAS staining, Grocott staining, and immunocytochemical staining to detect the cancer cell, wherein the cancer cell detected in method (a) and the cancer cell detected in method (b) are the same cancer cell.

16. The method according to claim 15, wherein the method (b) comprises Papanicolaou staining.

17. The method of claim 8, wherein step (a-3) comprises performing centrifugation to attach the cell mass to the cell-attaching region.

\* \* \* \* \*